US006653147B2

(12) United States Patent
DiCesare

(10) Patent No.: US 6,653,147 B2
(45) Date of Patent: Nov. 25, 2003

(54) APPARATUS AND METHOD FOR CHEMILUMINESCENT ASSAYS

(75) Inventor: Joseph L. DiCesare, Redding, CT (US)

(73) Assignee: Neogen Corporation, Lansing, MI (US)

(*) Notice: Subject to any disclaimer, the term of this patent is extended or adjusted under 35 U.S.C. 154(b) by 219 days.

(21) Appl. No.: 09/821,149

(22) Filed: Mar. 29, 2001

(65) Prior Publication Data

US 2002/0001822 A1 Jan. 3, 2002

Related U.S. Application Data

(60) Provisional application No. 60/193,519, filed on Mar. 31, 2000.

(51) Int. Cl.[7] ................. G01N 21/76; G01N 33/566; C12Q 1/66
(52) U.S. Cl. ............. 436/172; 436/501; 436/512; 436/518; 435/5; 435/7.1; 435/7.2; 435/8
(58) Field of Search ................ 435/4–6, 7.1, 7.2, 435/8; 436/501, 518, 523–525, 531, 533, 536, 538, 172

(56) References Cited

U.S. PATENT DOCUMENTS

| 3,764,713 A | * 10/1973 | Poplack et al. ............ 426/233 |
| 3,849,653 A | 11/1974 | Sakaide et al. ............ 250/361 |
| 3,933,592 A | 1/1976 | Clendenning ............ 195/103.5 |

(List continued on next page.)

FOREIGN PATENT DOCUMENTS

| EP | 0 038 134 B1 | 3/1981 |
| EP | 0 309 429 A2 | 9/1988 |
| EP | 0 439 525 B1 | 10/1989 |
| EP | 0 717 840 B1 | 8/1994 |
| GB | 2218803 A | 11/1989 |
| WO | WO 90/04775 | 5/1990 |
| WO | WO 95/07457 | 3/1995 |
| WO | WO 95/25948 | 9/1995 |
| WO | WO 97/23596 | 7/1997 |
| WO | WO 98/27196 | 6/1998 |
| WO | WO 98/49544 | 11/1998 |

OTHER PUBLICATIONS

Ford, Sharon et al; Improvements in the Application of Firefly Luciferase Assays: Methods in Molecular Biology, vol. 102: Bioluminescence Methods and Protocols, 1998.

Lundin, Arne; Optimised Assay of Firefly Luciferase With Stable Light Emission: Chemiluminescent and Bioluminescent Assays, 1993.

Wood, Keith, The Chemistry of Bioluminescent Reporter Assays: Promega Notes No. 65: 1998, p. 14.

(List continued on next page.)

Primary Examiner—Jill Warden
Assistant Examiner—Yelena Gakh
(74) Attorney, Agent, or Firm—Ian C. McLeod

(57) ABSTRACT

Disclosed herein are methods for the chemiluminescent assay of a variety of analytes of interest. The methods are adaptable to the determination of microbial species in both liquid samples and on solid surfaces. The disclosed methods can be used with rapid, self-contained chemiluminescence assay devices, or can be used with novel sampling devices and conventional microbial analysis techniques involving growth of microbial samples on appropriate culturing media. The specificity of the methods can be enhanced with the use of immunospecific reagents. The sensitivity of the technique can be increased by 3 to 6 orders of magnitude by first converting all DNA in the sample to inorganic phosphates before generating the emission signal. The breadth of applicability of the disclosed methods can be enhanced through the selection of appropriate enzyme-catalyzed reactions where one of the products of enzymatic oxidation is hydrogen peroxide.

32 Claims, 6 Drawing Sheets

U.S. PATENT DOCUMENTS

| | | | |
|---|---|---|---|
| 4,014,745 A | 3/1977 | Fletcher et al. | 195/103.5 K |
| 4,098,728 A | 7/1978 | Rosenblatt | |
| 4,144,134 A | 3/1979 | Plakas, Chris J. | 195/103.5 M |
| 4,246,340 A | 1/1981 | Lundin et al. | 435/8 |
| 4,353,868 A | 10/1982 | Joslin et al. | 422/101 |
| 4,672,039 A | 6/1987 | Lundblom | 435/291 |
| 4,689,305 A | 8/1987 | Stiffey et al. | 435/291 |
| 4,707,450 A | 11/1987 | Nason | 435/295 |
| 4,762,857 A | 8/1988 | Bollin, Jr. et al. | 514/777 |
| 4,818,883 A | 4/1989 | Anderson et al. | 250/361 |
| 4,833,075 A | 5/1989 | Vijayalakshmi et al. | 435/8 |
| 4,891,319 A | 1/1990 | Roser | 435/188 |
| 4,916,056 A * | 4/1990 | Brown et al. | 435/7.92 |
| 4,978,504 A | 12/1990 | Nason | 422/61 |
| 4,985,631 A | 1/1991 | Wannlund et al. | |
| 5,004,684 A | 4/1991 | Simpson et al. | 435/8 |
| 5,082,628 A | 1/1992 | Andreotti et al. | 422/82.08 |
| 5,124,254 A * | 6/1992 | Hewlins et al. | 435/28 |
| 5,139,933 A * | 8/1992 | Green et al. | 435/7.32 |
| 5,188,965 A | 2/1993 | Wannlund | 436/165 |
| 5,258,285 A | 11/1993 | Aegidius | 435/8 |
| 5,278,075 A | 1/1994 | Stone | 436/73 |
| 5,338,666 A | 8/1994 | Monthony et al. | 435/34 |
| 5,366,867 A | 11/1994 | Kawakami et al. | 435/8 |
| 5,396,325 A | 3/1995 | Carome et al. | 356/128 |
| 5,558,986 A | 9/1996 | Lundin | 435/4 |
| 5,580,785 A | 12/1996 | Stiffey et al. | 435/288.7 |
| 5,589,136 A | 12/1996 | Northrup et al. | 422/102 |
| 5,624,810 A | 4/1997 | Miller et al. | 435/8 |
| 5,624,815 A | 4/1997 | Grant et al. | 435/30 |
| 5,648,232 A | 7/1997 | Squirrell | 435/34 |
| 5,663,050 A | 9/1997 | Bedell | 435/7.23 |
| 5,760,406 A | 6/1998 | Powers | 250/461.2 |
| 5,770,391 A | 6/1998 | Foote et al. | 435/8 |
| 5,773,710 A * | 6/1998 | Squirrell | 73/28.01 |
| 5,783,399 A | 7/1998 | Childs et al. | 435/7.2 |
| 5,801,007 A | 9/1998 | Simpson et al. | 435/8 |
| 5,811,251 A | 9/1998 | Hirose, deceased et al. | 435/8 |
| 5,827,675 A | 10/1998 | Skiffington et al. | 435/8 |
| 5,891,656 A | 4/1999 | Zarling et al. | 435/792 |
| 5,902,722 A | 5/1999 | Di Cesare et al. | 435/4 |
| 5,905,029 A | 5/1999 | Andreotti et al. | 435/8 |
| 5,914,247 A | 6/1999 | Casey et al. | 435/34 |
| 5,916,802 A | 6/1999 | Andreotti | 435/287.7 |
| 5,917,592 A | 6/1999 | Skiffington | 356/244 |
| 5,965,453 A | 10/1999 | Skiffington et al. | 436/165 |
| 5,968,766 A | 10/1999 | Powers | 435/29 |
| 6,024,923 A | 2/2000 | Melendez et al. | 422/82.08 |
| 6,055,050 A | 4/2000 | Skiffington | 356/244 |

OTHER PUBLICATIONS

Lewis, Ricki, Refinements in Bioluminescence Assays Expand Technique's Applications; The Scientist 8 [5]:17, Mar. 7, 1994.

Colaco, Camilo et al; Extraordinary Stability of Enzymes Dried In Trehalose: Simplified Molecular Biology; Bio/Technology vol. 10; Sep. 1992, pp. 1007–1011.

Franks, Felix; Long–Tern Stabilization of Biologicals; Bio/Technology vol. 12 Mar. 1994; pp. 253–256.

Lappalainen, Juha, et al; Microbial Testing Methods for Detection of Residual Cleaning Agents and Disinfectants—Prevention of ATP Bioluminescence Measurement Errors in the Food Industry; Apr. 27, 1999; Journal of Food Protection, vol. 63, No. 2, 2000, pp. 210–215.

Lundin, A. et al; ATP Extractants Neutralised By Cyclodextrins; Clinical Research Centre, Karolinksa Institute, S–141 86 Huddinge, Sweden and BioThema AB, Strandvägen 36, S–130 54 Dalarö, Sweden; Amersham International plc, Cardiff Wales CF4 7YT, United Kingdom; pp. 399–402.

Mazzobre, M.F. et al; Combined effects of trehalose and cations on the thermal resistance of beta–galactosidase in freeze–dried systems; ; http://www.confex2.com/ift/99annual/abstracts/4344.htm; Jun. 22, 2000.

Miller, Danforth D., et al; Thermophysical Properties Of Trehalose and Its Concentrated Aqueous Solutions; Dec. 30, 1996; Pharmaceutical Research, vol. 14, No. 5, 1997; pp. 578–590.

Reilly, MJ et al; Factors Affecting the Shelf Life Of Freeze–Dried Firefly Luciferase Reagents; Biotrace Limited, The Science Park, Bridgend, Mid Glamorgan, CF31 3NA, UK; pp. 257–260.

Ribeiro, Angela R., et al; Immobilisation of Firefly Luciferase on Glass Strips as an Alternative Strategy for Luminescent Detection of ATP; Apr. 8, 1999; Luminescence Assays for Industry—Angela R. Ribeiro—Abstract; p. 1 of 1.

Velazquex, Madeline et al; Quenching and Enhancement Effects of ATP Extractants, Cleansers, and Sanitizers on the Detection of the ATP Bioluminescence Signal; Sep. 10, 1996; Journal of Food Protection, vol. 60, No. 7, 1997, pp. 799–803.

Wang, Chung–Yih et al; Interfacial Behavior of Firefly Luciferase; Department of Bioengineering, University of Utah, Salt Lake City, UT 84112, USA; pp. 99–103.

Wang, Chung–Yih et al; Purification and Preservation of Firefly Luciferase; Department of Bioengineering, 2480 MEB. University of Utah, Salt Lake City, UT 84112, USA; pp. 423–426.

Wang, CY et al; Surfactants And CoEnzyme A As Cooperative Enhancers Of The Activity Of Firefly Luciferase; Dept. of Bioengineering, University of Utah, SLC, UT 84112, USA; pp. 253–256.

* cited by examiner

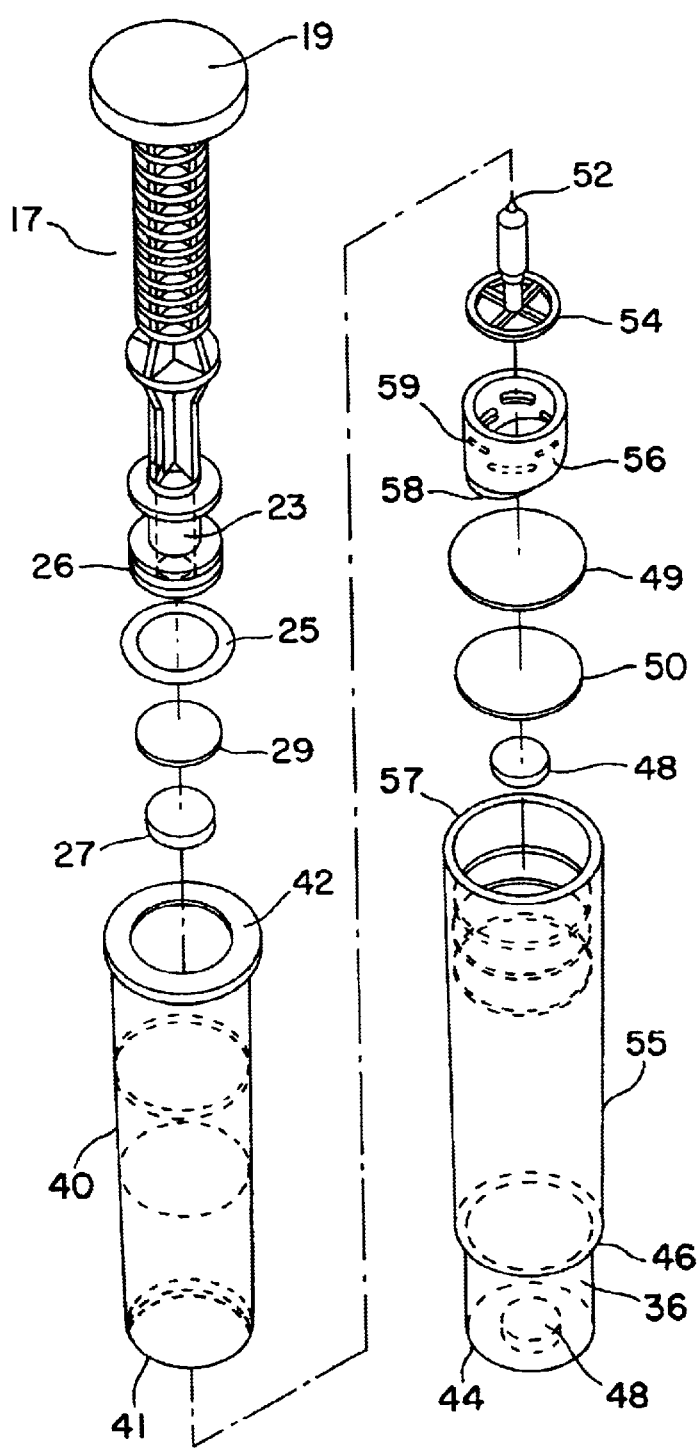
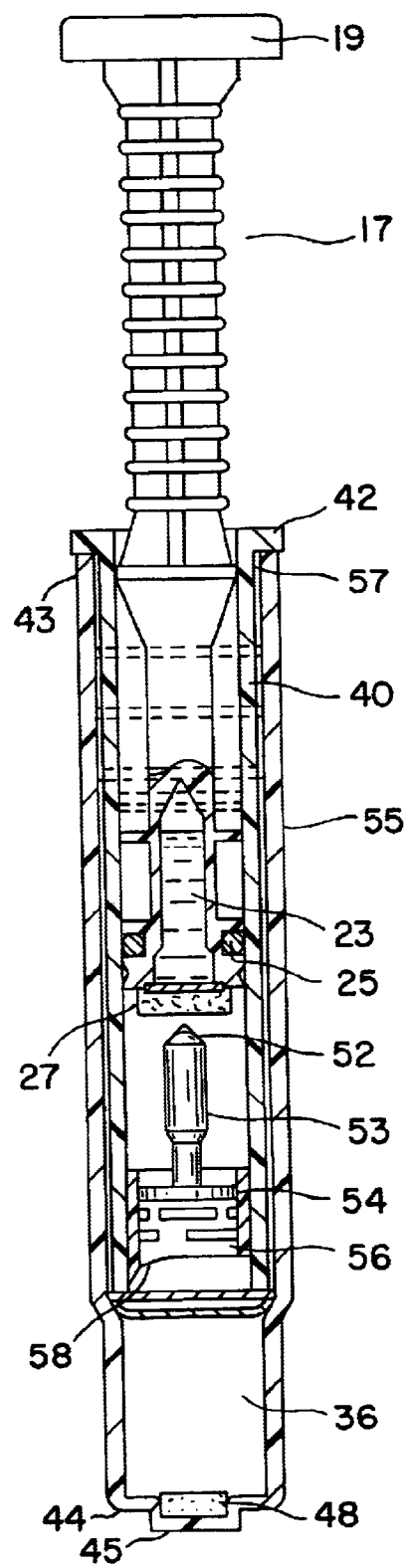
FIG. 4
FIG. 5

APPARATUS AND METHOD FOR CHEMILUMINESCENT ASSAYS

PRIOR APPLICATION

I claim priority benefits under 35 U.S.C. §119(e) of U.S. Provisional Patent Application Serial No. 60/193,519 filed Mar. 31, 2000.

FIELD OF THE INVENTION

This invention relates, in general, to methods and apparatus for the rapid and semi-automated assay of materials indicative of the presence of microbial species such as bacteria.

BACKGROUND OF THE INVENTION

The ability to rapidly and conveniently detect microorganisms is important for several industries, such as food preparation, medicine, beverages, toiletries, and pharmaceuticals. For example, the ability to detect bacterial contamination, particularly on surfaces, is paramount to improving safety in food processing and food service industries. During food processing, food can become contaminated with bacteria and then spoil. Furthermore, such contamination can be spread through contact of food with contaminated surfaces. Food poisoning can result if food contaminated with pathogenic bacteria, or its toxic products, is ingested without proper cooking. Public awareness of this potential problem is reflected in articles appearing regularly in the popular press. See, for example, Brody, J., "A World of Food Choices, and a World of Infectious Organisms," and "Clean Cutting Boards Are Not Enough: New Lessons in Food Safety," *The New York Times,* Jan. 30, 2001. In addition, spread of disease in hospitals and other facilities often occurs as a result of the passage of infectious microbes on the surface of clothes or equipment.

In light of this potential hazard, it is not enough to simply clean or sanitize a surface and assume it is free from microorganisms such as bacteria. Instead, there is a critical need to perform a test to detect whether the surface is actually free of microorganisms. Thus, random areas of a surface, such as a food preparation surface, can be tested for microorganisms to determine the general cleanliness of the surface.

One of the oldest methods to check for cleanliness involves culturing samples for bacteria. A test surface is chosen and wiped with a swab, and then the swab is smeared onto a culture medium. The medium is incubated and then checked for the presence of bacterial colonies grown in the medium. This is essentially the same type of procedure that is followed in the health services area when testing biological samples, such as a throat swab, for the presence of bacterial species such as streptococcus. Over the years, various types of culture media have been developed, along with numerous products based thereon. While the results of bacterial cultures are accurate, they are limited by the time that it takes to incubate the culture, usually on the order of days.

Unfortunately, such prior art methods for detecting bacterial contamination are too cumbersome and time consuming for immediate use by untrained workers. In particular, much more rapid bacterial assays are needed, particularly in slaughterhouses and food handling establishments. In these locations one must rapidly determine whether additional cleaning methods are required or whether proper safety procedures have been followed. Bacterial assays would be a useful component of a "hazards and critical control points program" (HCCP) to monitor and control bacterial contamination. However, typical bacterial assays based on cell culture techniques cannot provide results within a meaningful time frame.

In response for a need to obtain results more quickly, other methods for detecting microorganisms have been developed. The most productive area of development has focused on the detection of biomass on the test surface. Biomass includes living cells, dead cells, and other biotic products such as blood, and food residue. Biomass can be detected by an assay for ATP, adenosine triphosphate, a chemical found in all living organisms.

This assay is generally based on the "firefly" biochemical reaction that produces the characteristic bioluminescence associated with fireflies. The specific chemistry of this reaction will be discussed in more detail below. When appropriate reagents are mixed with a sample taken from a test surface, extracellular ATP immediately reacts and generates detectable chemiluminescence. However, intracellular ATP cannot be detected unless the ATP is first extracted from within the cells. Typically, this is accomplished by mixing the sample with an extraction reagent (releasing reagent) that extracts the ATP from within the cells or lyses the cells to permit access of ATP to chemiluminescent reagents. Typical extraction reagents are detergents. The extracted ATP then can be mixed with the luciferase/luciferin reagent to produce the observable reaction. It is important that the extraction reagent chosen does not inactivate the reagents. An additional consideration is the toxicity of the lysing agent, particularly when used on food preparation surfaces.

Chemiluminescent assays of ATP have traditionally been conducted using two basic types of systems: vial systems and all-in-one swab devices. A vial system uses a series of vials containing the reagents necessary to conduct the ATP tests. An all-in-one swab device provides all of the reagents and the swab in a self-contained apparatus.

In a vial system, for example, a first vial contains the extraction reagent, a second vial contains dried reagents, and a third vial contains a buffered solution. At the time of the test, addition of an appropriately buffered solvent from the third vial to the vial containing the reagents results in the re-hydration of the reagents.

Wiping a "Q-Tip®" type swab across the testing surface effectively samples whatever organisms may be present. Usually, the swab is pre-wetted with saline or an appropriate buffer solution. The swab containing the sample is placed in a test tube. Next, the proper amount of extraction reagent from the first vial is pipetted into the test tube containing the swab. After sufficient time has passed to ensure ATP extraction, the buffered solution containing hydrated reagent is pipetted into the test tube and the chemiluminescent reagents are allowed to react with the ATP. The test tube is then placed into a luminometer where the amount of light produced by the reaction is measured. If more than one sample is taken, each sample is placed in its own test tube.

Although vial systems can produce acceptable results, there are deficiencies. One significant problem is that the reagent solutions must be used within a short time of their preparation. If leftover solution is saved for later tests, the reagents will likely degrade and ultimately become ineffective, thus producing no reaction even in the presence of ATP (a false negative result). This problem is compounded by commercial producers of typical reagents that sell the reagent only in quantities that produce an amount of solution that is greater than that needed for individual tests. Furthermore, the alternative, dried reagents, can be relatively costly. Thus, the vial system results in waste of expensive reagents when only an individual test is required. Another shortcoming of vial systems is that accurate pipetting and mixing of reagents is required. A pipette is used to transfer the reagents from vial to vial or vial to tube. While pipetting can be highly accurate, it is laborious and time consuming. Also, if any of the vials or pipettes are not sterile, the biomass contained in them will produce a false positive for the presence of ATP. Furthermore, proper pipetting technique requires significant skill and experience, thus making consistent and accurate results difficult to attain without a relatively high degree of expertise on the part of the operator.

The all-in-one swab devices apply the same reaction as the vial systems but keep all of the reagents and swab in a self-contained apparatus that fits into a luminometer or, alternatively, can create a test solution that can be transferred (and transported) to a standard cell for a luminometer. More specifically, the all-in-one devices typically involve a swab that is placed in a plastic tube containing several chambers. An advantage to this system is that a unit dose of each reagent is provided for one test, thus avoiding waste of reagents when only one test is required. However, a certain procedure must be followed using an all-in-one device to ensure that the reagents are combined at the appropriate times and in the appropriate sequence.

In a typical all-in-one device, a swab pre-wetted with a wetting solution is placed in a sealed tube until ready for use. The wetting solution may contain an extractant. The sealed tube prevents evaporation of the wetting solution. At the appropriate time, the device is opened, the operator removes a pre-wetted swab, and collects a sample by wiping the swab along the testing surface. If present, the extractant will result in the release of intracellular ATP from the sample collected on the swab. The operator then places the swab back in the tube and the tube, once resealed, is ready for the ATP present in the sample to react with the chemiluminescence reagents.

Although numerous technologies have evolved in the implementation of all-in-one ATP assay systems, devices available to date have consistently displayed shortcomings rendering them less than ideal for use under the conditions most likely to be encountered. Examples in the prior art illustrate how others, with less than complete success, have approached the various problems discussed herein. For example, European Patent Application No. 0 309 429, entitled "Luminometric assay of cellular ATP," to Life Sciences International AB, discloses methods and an apparatus directed toward quantitation of biomass in a sample specimen. The disclosed apparatus comprises a reagent carrier and a fibrous sampling element (either separate or combined in a single structure), along with cuvettes containing a buffering solution into which the sampling element is placed for luminometric analysis. Due to the stated purpose of the device to obtain results for total bacterial biomass, the disclosed method comprises treatment of an aliquot of a liquid sample at elevated temperatures for a time sufficient to evaporate essentially all of the solvent medium for the purpose of degrading non-bacterial ATP from the sample. Also included in the apparatus and method is a calibration stick containing a known amount of ATP standard in a dried form. However, the disclosed apparatus and methods still suffer from considerable complexity and limited application, as the actual luminometric measurements giving rise to a biomass determination are contemplated to be performed on a laboratory-scale apparatus. Thus, the complexity of the process and the need for a full-scale laboratory apparatus imposes a requirement for operator skill and sophisticated equipment that renders the disclosed invention unsuitable for rapid, in situ analyses by untrained personnel in less-than-ideal field conditions.

PCT application WO 95/25948, entitled "Sample Collecting and Assay Device," to Celsis International PLC, discloses a hand-held sampling device comprising a glass tube with one or more reagent wells sealed by a frangible membrane or foil, as well as a sampling swab made from a suitably absorbent material. The disclosed use for the sampling device contemplates piercing one of the frangible seals with the sampling swab to moisten the swab, sampling a surface to be analyzed with the moistened swab, returning the swab with sample to the device and further puncturing the remaining one or more frangible seals to expose the swab with sample to reagent solutions contained therein. The sampling device, wherein the swab has been exposed to reagent solutions, can then be placed, after a suitable period of incubation, in a luminometer to measure the level of chemiluminescence from the sample, although the reference fails to disclose details of the type or construction of the luminometer. Alternatively, the sampling device may comprise a single reservoir with a frangible seal, wherein the reservoir contains a wetting solution only. It is clear that the disclosure is directed solely toward the sampling device only and contemplates measurement of chemiluminescence collected with the device of the invention in a conventional, laboratory-scale instrument, specifically adapted to hold the sampling device or to receive sample-containing solutions from the device. Thus, the disclosed invention, due to the relative complexity of the multi-compartment sampling device using reagents in solution form, along with the need for a relatively sophisticated measurement instrument is not ideally suited for use by untrained operators in the relatively harsh conditions of a field environment.

PCT application WO 98/27196, entitled "Sample-Collecting and Assay Device," to Celsis International plc, discloses a hand held sampling device with a pen-type configuration. The sampling device comprises a fluid reservoir with a frangible seal, which seal may be broken by the inward depression of a top portion of the device, releasing wetting solution that travels downward through an internal portion of the device, wetting a conventional absorbent swab. The swab may then be removed to sample a surface and returned to the device. Thereafter, a bottom cuvette portion is pressed upward breaking a frangible seal between the swab-containing central portion of the device and the bottom cuvette portion and releasing fluid from the central portion into the cuvette portion. The cuvette portion may contain further reagents in dried form. A window in the cuvette wall permits visual inspection of a color developed by a reaction between sample and reagents. Alternatively, light may be emitted from the sample by ATP-chemiluminescence. However, as with WO 95/25948, the application does not disclose details of the luminescence measuring device, although the implication is clear that the device would be a laboratory-scale instrument, perhaps adapted to receive the disclosed sampling device.

U.S. Pat. Nos. 5,827,675 and 5,965,453, both entitled "Test Apparatus, System and Method for the Detection of Test Samples," Skiffington and Zomer, inventors, and assigned to Charm Sciences, Inc., disclose a multi-component sampling device designed to be used with a desktop analytical luminometer. The sampling device is comprised of a cover portion into which is removably secured a "Q-Tip®" style swabbing stick with an absorbent material on one end. In operation, the cover and swab are removed from the central portion of the sampling device and the tip of the swab, presumably after being wetted with an external solution, is rubbed across a surface to be analyzed. The swab is then returned to the sampling device where the portion of the device containing the swab is moved downwardly within the device, rupturing frangible seals between sequential reagent-containing reservoirs. Continued downward movement results in the swab tip being immersed in the reagent solutions released from the storage reservoirs in a microtube test unit that forms the bottom component of the sampling device. This test unit may also contain a reagent tablet that, upon contact with the solutions from the ruptured storage reservoirs releases reagents necessary to generate the analytical signal. The microtube test unit is then removed from the sampling device, sealed with an aluminum seal stored on the external surface of the device and transported to the desktop analytical instrument where either color or a luminescent signal is recorded. Although offering a number of advantages over prior art methods and devices, the invention disclosed in this reference still suffers from the drawbacks of a somewhat complex internal structure to the sampling device, and the extensive handling required to remove the microtube from the bottom of the device and seal the same before being transported to a separate desktop analytical device for actual measurement.

In a series of applications (see EP 0 717 840 B1; EP 0 439 525 B; WO 95/07457; and WO 90/04775), Biotrace Ltd. has disclosed, generally, a test kit comprising a luminometer and a sampling device for determination of bacteria and other living cells for an assessment of hygienity. The kit comprises a luminometer with a photodetector, wherein the detector is an avalanche photodiode; a plurality of pipettes and pipette tips, sample vessels, sterile swabs, and containers of reagents for fluorescence or luminescence reactions. The cuvettes may also contain appropriate enzymes in a dried form for the chemiluminescent or fluorescent reactions. In operation, a sterile swab is removed from its packaging, wiped across a surface to be analyzed, and returned to a pipette tip. The pipette tip is then attached to a pipette, and the pipette is used to draw a predetermined exact volume of appropriate reagent solution, such as a solution containing a lysing agent, into the pipette. The resultant mixture is allowed to incubate for a suitable period of time. The reagent within the pipette is then transferred to a cuvette, where the solution is withdrawn back into the pipette and then re-transferred to the cuvette a number of times in order to ensure adequate mixing. The cuvette is then placed in the luminometer where emission is measured. Although the invention disclosed in these applications offers some advantages over other prior art methods and devices, in that the kit of the invention comprises a portable analytical device, the invention as a whole still presents some significant shortcomings. Principal among these is the relative complexity of the process by which a sample swab interacts with the reagents necessary to develop an analytical signal. As one of skill in the relevant art would recognize, there is a considerable amount of skill required in the manipulation of pipettes and other such transfer glassware in order to insure proper preparation of resulting solutions. Thus, the disclosed invention would likely not be ideally suited for use by untrained operators in the harsh and variable conditions found in the field.

U.S. Pat. No. 4,978,504, entitled "Specimen Test Unit," to Nason, discloses, in general, a sample collection device adapted for applications involving chemiluminescence assays. The disclosed sample collection device comprises a cap portion to which is attached an elongated swab, the distal tip of which comprises a "Q-Tip®" style absorbent material. The cap portion also contains a storage well in which is a frangible glass ampoule within which is stored a suitable reagent, or other, solution. The storage well is separated from the distal swab portion by a porous filter disk. Alternatively, the filter disk may be impregnated with additional reagents. In operation, the cap portion is removed from the device and the swab tip is used to collect sample from a surface to be analyzed. The cap and swab assembly is then returned to the sampling device. The top-most portion of the cap is then squeezed or otherwise deformed so that the reagent-containing ampoule is broken to release its contents to flow downwardly through the device to the swab tip. The filter disk effectively permits the flow of solution without permitting the passage of remnants of the broken ampoule. If the filter disk is impregnated with additional reagents, then these presumably mix with the fluid contents of the ampoule as that fluid flows downwardly through the device. The solution/reagent mix flows over the swab tip and collects in the bottom portion of the sampling device. At this point, the sampling device may be inserted into an analytical instrument for a determination of the luminescence from the sample, but the reference does not disclose details on the type or construction of such a device. Presumably, such an instrument would be a laboratory-scale device. Alternatively, the sampling device can be used to transport the sample/reagent to a cuvette or other sample cell for analysis in a conventional instrument. As with other examples of the prior art, this reference exhibits shortcomings in overall design that render it incapable of meeting the ideal criteria for such a device articulated herein. For example, the device is somewhat complex in design and manufacture and requires the use of glass ampoules as reagent reservoirs. Given the likely storage and use of such a sampling device in the field, such constructions are less than ideal.

U.S. Pat. No. 4,672,039, entitled "Apparatus for Registering the Presence of Bacteria, Particularly in Field Conditions," Lundbloom, inventor, and assigned to AB Sangtec Medical, discloses a portable field-test apparatus for the detection of a threshold level of bacteria in samples. The device is designed to receive an injection of a liquid sample suspected of harboring bacterial organisms onto a filter portion of the device. The bacteria so introduced to the device then have a series of reagent solutions sequentially sprayed upon them, the solutions comprising sodium hydroxide, luminol and perborate in precise amounts. An opening in the device is then closed and a transparent window portion permits chemiluminescence from the sample to impinge upon a light recording means that is preferably a piece of photographic, Polaroid-type, film. Although the disclosed device is presumably capable of use under field conditions, the complex process of the sequential spraying of specific amounts of different reagents, the need to utilize a liquid sample and the requirement for a light-tight environment imposed by a photographic film detector all represent significant departures from an ideal configuration or method of use.

U.S. Pat. No. 4,353,868, entitled "Specimen Collecting Device," Joslin and Dennison, inventors, assigned to Sherwood Medical Industries, Inc., discloses, generally, a sampling device. The disclosed invention comprises a multi-part sampling device with a top cap portion to which is attached a "Q-Tip®" style swabbing stick with an absorbent material on one end, and a container portion that houses a solution reservoir. The solution reservoir is separated from the upper body of the container portion by a frangible seal. In use, the upper cap portion is removed and the exposed swab tip is used to swipe a surface suspected of bacterial contamination. The cap portion is then returned to the device wherein a downwardly directed force ruptures the membrane covering the solution reservoir and immerses the swab tip into the solution contained therein. The sample exposed to the reagent solution within the device may then be transported to a laboratory environment where the solution may be subsequently transferred to an appropriate sample cell or cuvette for analysis in a laboratory-scale instrument. However, the relatively short time over which emission of measurable luminescence will occur from the sample is such that the time between the rupture of the reservoir seal to transfer of the resulting solution to an analytical instrument must be rather short. It is clear from the disclosure of this reference that the invention is suited solely for collection and transport of samples to an analytical facility with the capability for accurate fluorescence measurements. Thus, although the sampling device may be used in the field, there must necessarily be a substantial passage of time from collection of a sample in the field to receipt of actual analytical results.

U.S. Pat. No. 5,624,810, entitled "Method for the Detection of Surfaces Contaminants," Miller and Loomis, inventors, and assigned to New Horizons Diagnostics Corp., discloses a sample collection device for use in a method to detect the presence of bacteria in a sample. The reference discloses that sample collection can be by means of a "Q-Tip®)" style swabbing tip or, alternatively, by means of small absorbent sponges. In practice, the swabbing tip or sponge is wet with a wetting solution and contacted with a surface suspected of bacterial contamination. The swabbing device or sponge is then transferred to a reservoir of collection fluid wherein the sampling material is intimately mixed with the fluid. In the case of the use of sponges for sample collection, the reservoir of collection fluid is physically manipulated to facilitate the mixing of sample with the collection fluid. For a flexible plastic reservoir as disclosed in the reference, the physical manipulation comprises repeated squeezing or wringing out of the sponge within the reservoir. The disclosed method contemplates the use of a large volume concentration apparatus into which is delivered the extraction fluid from the external reservoir after mixing with the sampling device. The bacterial cells in the concentrated sample are then lysed and the resultant mixed with appropriate chemiluminescence reagents. A volume of the ATP-containing fluid is then transferred to an appropriate instrument for measurement of emission intensity. It would be apparent to one of skill in the relevant art that such an apparatus and method involves considerably more complexity than would be suitable for use under field conditions by an unskilled operator. Thus, the teachings of the reference fall far short of attaining the goals of an ideal apparatus or method for hygiene monitoring.

In U.S. Pat. No. 5,783,399, entitled "Chemiluminescent Assay Methods and Devices for Detecting target analytes, Childs et al., inventors, and PCT application WO 08/49544, entitled "Hand-Held Luminometer," McClintock et al., inventors, both assigned to Universal Healthwatch, Inc., there are disclosed a sampling and luminescence developing device, and a hand-held luminometer in which to read the luminescence signal so generated. The references disclose a sample collection and signal development device comprising an absorbent material, such a filter paper, for collection of samples and a second absorbent material for loading with appropriate reagents for the generation of a chemiluminescence signal. Alternatively, the device may combine the sample collection and reagent storage portions in a single structure of absorbent material. The device may also contain a reservoir of carrier liquid. Upon collection of a sample by wiping the absorbent material on the surface to be analyzed, a carrier fluid is applied from the reservoir to the absorbent material and, by wicking action, travels horizontally along the thin strips of absorbent material. The movement of the carrier fluid by capillary action through the absorbent material results in the migration of sample and/or reagent to a reaction zone wherein a chemiluminescent reaction may take place. The emission generated by such reaction is released from the device through a form of transparent window and subsequently impinges upon the detector portion of a luminometer. The luminometer disclosed by the references comprises a handle portion and a head portion, the head portion further comprising one or more electronic components of the device, such as a display. The device also comprises a sample section designed to receive the sampling and luminescence development device described immediately above. Alternatively, the sample section may work with a cuvette inserted into the section, the cuvette containing a fluid sample for analysis. The means included in the device for detection of a luminescence signal may comprise a photomultiplier tube, a charge coupled device (CCD), or a photon counting device. The preferred signal detection means is a photomultiplier tube (PMT), such as a Mamamatsu H5773. Although the disclosed devices offer a number of improvements over the prior art sampling and detection devices, the use of the sampling device remains somewhat complex in the requirement for application of a carrier fluid to the sampling device in order to effect contact of the sample with the necessary chemiluminescent reagents. One of skill in the art would appreciate the variations potentially introduced through the need to handle and deliver the carrier fluid.

SUMMARY OF THE INVENTION

In a first embodiment, the present invention provides a method for assaying for the presence of an analyte of interest, the method comprising the steps of (a) loading a sampling swab with a first reagent solution comprising a reagent and a solvent; (b) contacting a substance to be analyzed with the swab so as to obtain a sample of at least a portion of the analyte of interest, if any, present in the substance; (c) transferring the sample from the sampling swab to a receptacle; (d) contacting the sample with a reactant mixture in the receptacle to induce a chemiluminescent reaction; and (e) measuring the emission of chemiluminescent radiation from the reaction to indicate the presence or absence of the analyte of interest in the sample. Preferably, the analyte of interest comprises cellular material. In one aspect, the method of the present invention contemplates transferring the sample to the receptacle by contacting the sampling swab with a second reagent solution so as to rinse the sample from the swab and into the receptacle. Preferably, the first reagent solution comprises a detergent. More preferably, the detergent is benzalkonium chloride.

In another aspect, the method of the present invention contemplates the use of a first reagent solution comprising a sterile saline solution. Preferably, the first reagent solution is loaded into the sampling swab by contacting the swab with the solution so that the swab absorbs a volume of the solution corresponding to no more than 50% to 80% of a saturation loading for the swab. Alternatively, the first reagent solution is loaded into the sampling swab by contacting the swab with the solution and then evaporating the solvent from the solution. Preferably, the analyte of interest is present in a liquid substance. Alternatively, the analyte of interest is present on a solid surface.

In another aspect, the method of the present invention provides for a receptacle that contains a culture medium suitable for promoting microbial cell growth. In yet another aspect, the reactant mixture comprises a luciferase/luciferin system. Preferably, herein the reactant mixture comprises a firefly luciferase system. Alternatively, the reactant mixture comprises a recombinant luciferase system In another embodiment, the method of the present invention includes the additional step of filtering the liquid substance through a filter medium effective to remove microbial species from the substance to create a microbial filtrate on the filter medium before contacting the reagent swab with the microbial filtrate.

In yet another embodiment, the method of the present invention contemplates a reactant mixture comprising reagents that break down all nucleic acids present in the sample to inorganic phosphates and convert the inorganic phosphates to adenosine triphosphate (ATP).

In still another embodiment, the method encompasses an analyte of interest comprises a species that can be oxidized by the action of an enzyme to yield an oxidized form of the species and hydrogen peroxide. Preferably, the analyte of interest is selected from the group consisting of sugars, lipids, alcohols, amino acids, amines, and the reduced form of nicotine adenide dinucleotide (NADH). In one aspect, this embodiment of the invention provides for a reactant mixture comprising an enzyme capable of oxidizing the analyte of interest to an oxidized form and hydrogen peroxide, and reagents capable of reacting with hydrogen peroxide to produce a chemiluminescence emission.

In still another embodiment, the receptacle used in the practice of the method of the present invention contains an immunospecific species capable of binding to the analyte of interest. Preferably, the immunospecific species is bound to a solid surface within the receptacle. More preferably, the immunospecific species is bound to microspheres. In a specific aspect of the practice of the method of the present invention, the method comprises the additional step of removing all species present in the receptacle that are not bound to the immunospecific species before contacting the sample with a reactant mixture. Preferably, the immunospecific species is an antibody to the analyte of interest or an antigen to the analyte of interest. Alternatively, the analyte of interest is an antibody.

BRIEF DESCRIPTION OF THE DRAWINGS

FIG. 4 is an exploded view of the sampling/analysis member of the device of FIG. 1.

FIG. 5 is a cross-sectional view of the sampling/analysis member of the device of FIG. 1.

DETAILED DESCRIPTION OF THE INVENTION

Figure 1:
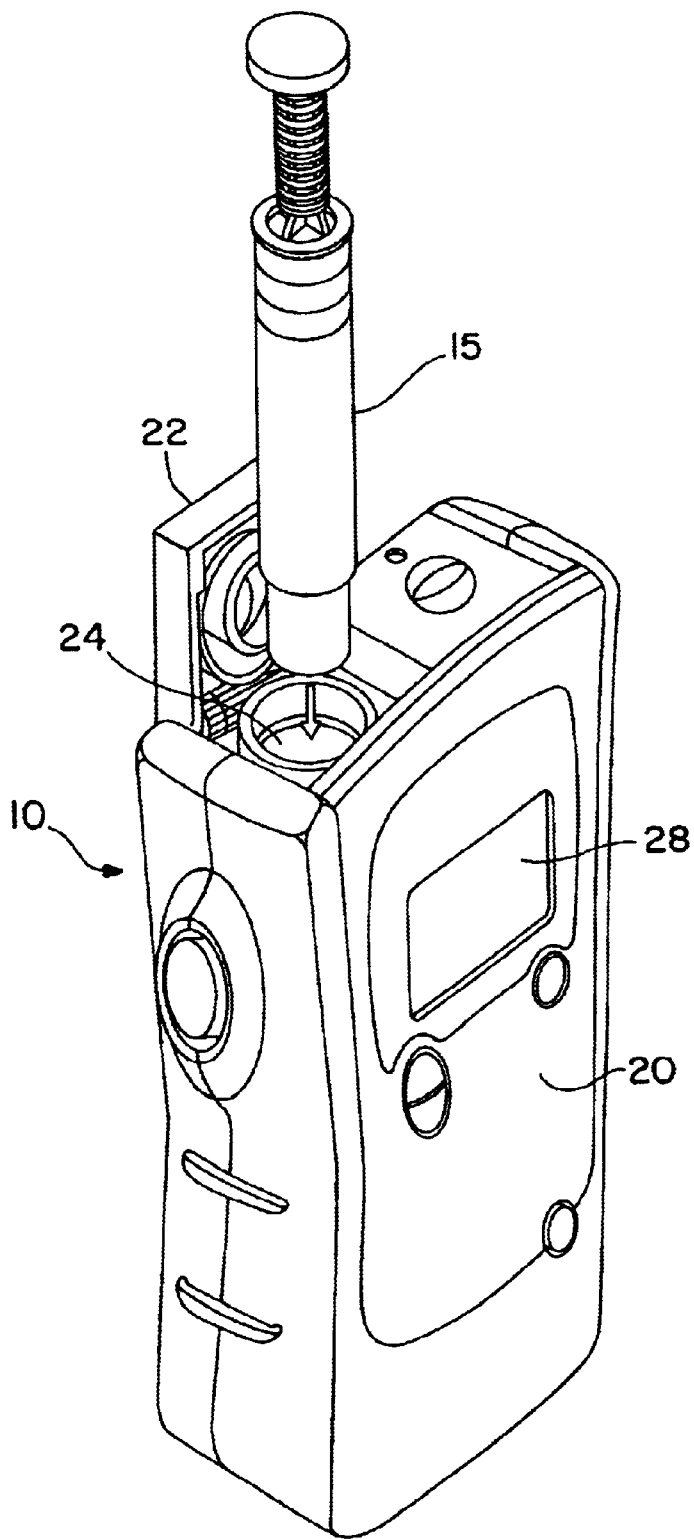
FIG. 1 is a perspective view of the analytical device of the present invention.

In general, the present invention provides an apparatus and methods that make possible the rapid detection through chemiluminescence of materials indicative of the presence of microbial species, including bacteria, on a surface. The present invention is capable of use by unskilled operators under the relatively harsh field environment of institutional food preparation services, health care providers and the like.

Bioluminescence refers to the visible light emission in living organisms that accompanies the oxidation of organic compounds such as luciferins, mediated by an enzyme catalyst, such as luciferase. Luminescent organisms, which include bacteria, fungi, fish, insects, algae, and squid, have been found in marine, freshwater, and terrestrial habitats, with bacteria being the most widespread, and abundant, luminescent organism in nature. Although their primary habitat is in the ocean in free-living, symbiotic, saprophytic or parasitic relationships, some luminescent bacteria are found in terrestrial or freshwater habitats. The enzymes involved in the luminescent (lux) system, including luciferase, as well as the corresponding lux genes, have been most extensively studied from the marine bacteria in the Vibrio and Photobacterium genera and from terrestrial bacteria in the Xenorhabdus genus, in particular the *Vibrio harveyi, Vibrio fischeri, photobacterium phosphoreum, Photobacterium leiognathi,* and *Xenorhabdus luminescens* species. It has been found that the light-emitting reactions are quite distinct for different organisms, with the only common component being molecular oxygen. Therefore, significant differences have been found between the structures of the luciferases and the corresponding genes from one luminescent organism to another.

Chemiluminescent reactions can be used in various forms to detect bacteria in fluids and in processed materials. In the practice of the present invention, a chemiluminescent reaction based on the reaction of adenosine triphosphate (ATP) with luciferin in the presence of the enzyme luciferase to produce light provides the chemical basis for the generation of a detectable analytical signal. Since ATP is present in all living cells, including all microbial cells, this method can provide a rapid assay to obtain a quantitative or semi-quantitative estimate of the number of living cells in a sample, or on a sample surface. Early discourses on the nature of the underlying reaction, the history of its discovery, and its general area of applicability, are provided by E. N.

Harvey (1957), *A History of Luminescence: From the Earliest Times Until* 1900, Amer. Phil. Soc., Philadelphia, Pa.; and W. D. McElroy and B. L. Strehler (1949), *Arch. Biochem. Biophys.* 22:420–433.

ATP detection is a reliable means to detect bacteria and other microbial species because all such species contain some ATP. Chemical bond energy from ATP is utilized in the bioluminescent reaction that occurs in the tails of the firefly *Photinus pyralis*. The biochemical components of this reaction can be isolated free of ATP and subsequently used to detect ATP in other sources. Alternatively, the genes producing the proteins that participate in the bioluminescent reaction can be isolated, cloned into a suitable expression system, and used to produce a recombinant form of the luminescent reactants. Examples of such techniques are disclosed in U.S. Pat. No. 5,741,668, the specific disclosure of which is hereby incorporated by reference. The mechanism of this firefly bioluminescence reaction has been well characterized (DeLuca, M., et al., 1979 *Anal. Biochem.* 95:194–198). Of note is that luciferase-based assays differ from most familiar enzyme-based analytical determinations. Most enzyme-based assays monitor either the production of a product or the disappearance of a substrate. Usually, the compound measured is stable so that its concentration can be determined after a specific time. At low adenosine 5'-triphosphate (ATP) concentrations, however, the kinetics of the luciferase reaction approach pseudo-first order behavior.

In the case of the luciferase reaction, AMP, $PP_i$, $CO_2$, and oxyluciferin are typical products that accumulate, but the product that provides the analytical signal is light. The two-step luciferase reaction sequence is shown below. Step one forms an enzyme-bound luciferyl adenylate. Either Mg-ATP or $LH_2$ (luciferin) can add first to the enzyme LUC.

$$LH_2 + MgATP + LUC \rightarrow LUC\text{-}LH_2\text{-}AMP + MgPP_i \quad (1)$$

Step two is the oxidative decarboxylation of luciferin with the production of light on decay of the excited form of oxyluciferin.

$$LUC\text{-}LH_2\text{-}AMP + O_2 + OH^- \rightarrow LUC\text{-}OL + CO_2 + AMP + light\ (550\text{–}570\ nm) + H_2O \quad (2)$$

The oxyluciferin product, OL, is released slowly from the enzyme-product complex. This gives the flash kinetic pattern observed with high ATP concentrations, not typically encountered under conditions of practice of the present invention, under which conditions the luciferase acts catalytically. The initial flash of light emission observed with high ATP concentration is owing to a "first round" of enzyme activity. This flash rapidly decays to a relatively constant light emission, similar to that seen at low ATP concentrations, which is thought to be the result of the enzyme slowly turning over by releasing the oxyluciferin.

Turning now to the Figures, there is provided in FIG. 1 an illustration of the hand-held automatic chemiluminescence assay device of the present invention, shown generally at 10. Shown in FIG. 1 is the sampling/analysis member 15, and the hand-held luminometer 20, designed to accept the sampling/analysis member 15. As can be seen from FIG. 1, and the following Figures, the luminometer 20 of the present invention is of a scale that can easily fit into an operator's hand, making possible essentially single-handed operation. The sampling/analysis member 15 can be held in one hand and easily inserted in the sample port 24 of the luminometer as the operator holds the device in the operator's other hand. Once the internal electronics of the luminometer 20 are in a ready state, full insertion of the sampling wand 17 into the assembly already inserted into the luminometer brings the chemiluminescent reaction into close proximity to the luminometer's detector circuitry (not shown). A digital readout is then displayed on the luminometer's display screen 28. The readout displayed on the screen informs the operator of the relative hygienity of the sampled surface based upon the detection of chemiluminescence indicating the presence of ATP from microbial cells. For further details regarding the mechanical and electronic structure of the luminometer device of the present invention, the reader is referred to co-pending application Ser. No. 09/821,571, filed Mar. 29, 2001. The disclosure of which is hereby specifically incorporated by reference.

Figure 2:
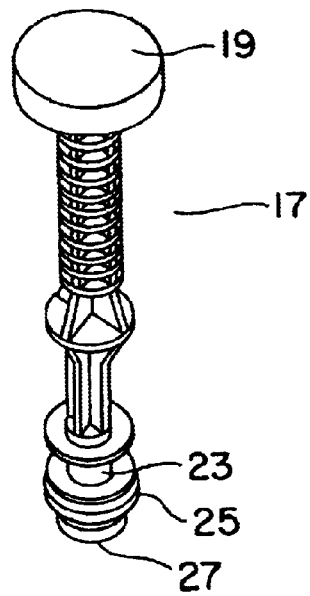
FIG. 2 is a perspective view of the sampling wand of the device of FIG. 1.
Figure 3:
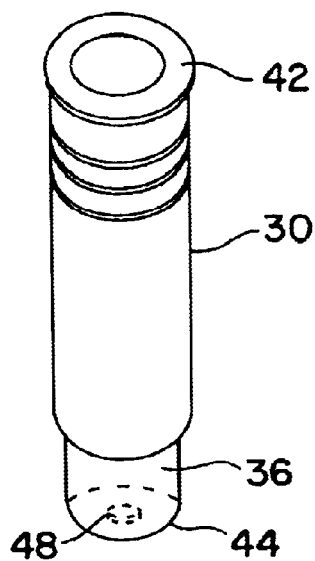
FIG. 3 is a perspective view of the analysis structure of the device of FIG. 1.

By reference to FIGS. 2 and 3, the sampling/analysis member 15 is depicted to illustrate two of the component structures of the member. FIG. 2 illustrates the sampling wand component 17 of the sampling/analysis member 15. The sampling wand 17 is further comprised of a top 19 located at the proximal end of the wand. The primary purpose of the top 19 is to provide a structure that facilitates the operator's manipulation of the sampling wand 17 as the wand is moved between specific positions within the inner chamber (not illustrated) of the sampling/analysis member 15. Although FIG. 2 illustrates the top 19 in a substantially flat cylindrical shape, it will be appreciated that this shape is for illustrative purposes only, and that other, equally useful, geometries are possible and within the grasp of one of ordinary skill in the appropriate art.

Also illustrated in FIG. 2 are additional structural elements of which the sampling wand 17 is comprised. These include a reagent reservoir 23 located toward the distal end of the sampling wand 17. This reservoir is of approximately 200–250 $\mu L$ in total volume. As will be discussed in greater detail below, the contents of this reservoir that, in one embodiment, comprise a buffered neutralizing solution, are released into the inner chamber (not illustrated) of the sampling/analysis member by piercing structures located within that inner chamber. The sampling wand 17 further comprises a polymeric swab disc 27 adhered to the exterior of the distal end of the sampling wand 17, and on a common vertical axis with the wand. Also illustrated in FIG. 2 is an o-ring structure 25 located toward the distal end of the wand 17, and situated on the exterior of the cylindrically shaped distal portion. The purpose of the o-ring 25 is to provide a sealing fit between the outer surface of the distal portion of the wand 17 and the inner surface of the inner chamber (not illustrated) of the sampling/analysis member 15, as the wand 17 moves longitudinally through the inner chamber. It is preferred to achieve such sealing fit between the wand 17 and the inner chamber in order to prevent the drying out of the pre-wetted sampling swab 17.

Turning to FIG. 3, there is illustrated the analysis structure 30 of the sampling/analysis member 15 of the device of the present invention. The analysis structure 30 is substantially cylindrical in shape and is actually comprised, in the embodiment illustrated in FIG. 4, of two separate but mating components, an inner chamber 40, and an outer chamber 55. As will be recognized by one of skill in the appropriate art, the use of two separate structures in the sampling/analysis member is dictated more by manufacturing concerns than by operational factors and that the present invention contemplates a device that may be constructed of a single chamber. Located at the distal end of the outer chamber 55 of the analysis structure 30 is a reaction well 36 that, as is apparent from FIGS. 3–5, is co-linear along the same central axis as the inner chamber 40 and the analysis structure 30. The diameter of the cylindrically shaped reaction well 36 is slightly smaller than the diameter of the outer chamber 55. The point of juncture between the walls of the outer chamber 55 and the slightly narrower walls defining the reaction well 36 portion of the outer chamber form a shoulder region 46, best seen in FIGS. 4 and 5. In the bottom wall 44 of the reaction well 36 is a reagent disc cavity 45, best seen in FIG. 5, and seen in hidden lines in FIG. 3. The reagent disc cavity 45 holds the reagent disc 48, the composition of which is discussed in more detail below. Also illustrated in FIG. 3 is the top rim 42 of the inner chamber 40. As is best illustrated in FIGS. 4 and 5, the bottom edge 43 of the top rim 42 of the inner chamber, in the fully assembled arrangement of the sampling/analysis member 15, rests on the top edge 57 of the outer chamber 55.

FIG. 4 illustrates the sampling/analysis member 15 of the device of the present invention in an exploded view. Part numbers are consistent with the part numbers referenced in FIGS. 1–3 for identical structural elements, a convention adhered to throughout this description. Starting from the top, or proximal, end of the sampling/analysis member, there is shown a top 19 of the sampling wand 17. Toward the distal end of the sampling wand 17, there is shown the reservoir 23, and the o-ring channel 26. Immediately below the distal end of the sampling wand 17, there is shown the o-ring 25 that sits in the o-ring channel 26 to provide, as discussed above, a sealing fit between the sampling wand 17 and the inner walls of the inner chamber 40. Shown immediately below the o-ring is the upper seal 29 that sits on the lower edge/surface (not shown) of the distal end of the sampling wand 17. The seal 29 is made of a frangible material, preferably aluminum foil coated to improve chemical resistance, and is adhered through use of an appropriate adhesive to the bottom edge/surface of the sampling wand 17. The seal 29 serves to seal the reagent solution within the reservoir 23, and to prevent the diffusion of species from the reservoir across the membrane as would likely be the case with non-metallic seals. The next component illustrated in FIG. 4 is the polymeric sampling swab 27, the composition of which is discussed in more detail below. The sampling swab 27 is affixed to the bottom of the sampling wand 17, with the upper seal 29 interposed between it and the reagent reservoir 23.

The next component illustrated in FIG. 4 is the inner chamber 40 of the sampling/analysis member 15. The inner chamber 40 is cylindrical in shape and sized to fit snugly within the outer chamber 55, also shown in FIG. 4. Located at the proximal end of the inner chamber 40 is the top rim 42. At the distal end of the inner chamber is the bottom edge 41. As can be seen in FIG. 4, the cylindrically shaped inner chamber 40 is open at both ends. The top, or proximal, end of the inner chamber is effectively closed by the bottom of the sampling wand 17, through the sealing effect of the o-ring 25 as it contacts the inner walls of the inner chamber 40. The bottom, or distal, end of the inner chamber 40 is sealed by a first seal 49, as seen on the right side of FIG. 4, affixed with an appropriate adhesive to the bottom edge 41 of the inner chamber. Like the upper seal, the first seal 49 is composed of a frangible material, preferably aluminum foil.

Moving to the right side of FIG. 4, there is shown, at 53, a piercing member, comprised of a circular base 54 at the distal end, and a point 52, at the proximal end. Immediately below the piercing member 53 is the cutting member 56, which is substantially cylindrical in shape. Each end of the cutting member 56 is open, and the distal, or bottom, edge of the cutting member, the cutting edge 58, is angled so that the top edge is not parallel to the cutting edge. Also illustrated is the base channel 59 that is circumferentially positioned within the cutting member 56. The base 54 of the piercing member 53 rests within the base channel 59 so that, when the sampling/analysis member 15 is fully assembled, as is illustrated in FIG. 5, the piercing member 53 sits within the cutting member 56, which, in turn, sits within the inner chamber 40 of the sampling/analysis member 15. The central axis of the piercing member 53 is co-extensive with the central axis of the cutting member 56, the inner chamber 40, and the outer chamber 55 of the sampling/analysis member 15.

Second seal 50 is affixed through the use of an appropriate adhesive to the shoulder region 46 of the outer chamber 55. However, in an alternative embodiment of the device, the outer chamber can be constructed without the second seal 50. Manufacturing concerns, rather than operational concerns, will frequently dictate the use of both first 49 and second 50 seals. The final component of the sampling/analysis member 15 illustrated in FIG. 4 is the reagent disc 48. As is illustrated by the hidden lines at the distal end of the outer chamber 55, the reagent disc 48 sits within a reagent disc cavity 45 (best seen by reference to FIG. 5) in the bottom of the reaction well 36.

FIG. 5 provides a cross-sectional view of the fully assembled sampling/analysis member 15 prior to use. By reference to FIG. 5, it will be possible to gain an appreciation of the relative positioning of the individual components of the member 15 in this assembled state. In this state, the bottom edge 41 of the inner chamber 40 rests on the shoulder region 46 of the outer chamber 55, toward the distal end of that chamber. Also apparent are the first 49 and second 50 seals positioned on the bottom edge 41 of the inner chamber and the shoulder region 46 of the outer chamber, respectively. By reference to FIG. 5, it can be seen that the cutting member 56 is positioned within the inner chamber 40 so that the distal cutting edge 58 is positioned directly above the first and second seals, 49 and 50. In the assembled state, the piercing member 53 sits with its base 54 situated within the cutting member 56, specifically within the base channel 59 of the cutting member. In the fully assembled arrangement, the point 52 of the piercing member 63 is positioned immediately below the sampling swab 27. Immediately above the sampling swab 27, on the proximal side of the upper seal 29, is the reagent reservoir 23 in the sampling wand 17. As provided in the assembled configuration, the sampling/analysis member 15 may be provided with an external seal (not shown) that serves as a vapor barrier preventing loss of reagent or wetting solution from within the device.

Figure 6:
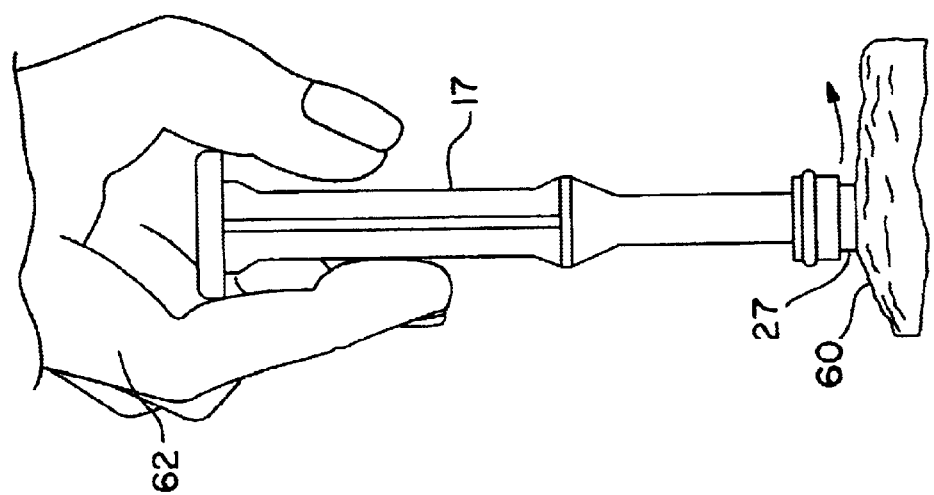
FIG. 6 is an illustration of the sampling wand of the device of FIG. 1. sampling a surface suspected of bacterial contamination.

Referring now to FIGS. 6 through 9, there is illustrated the sequential operation of the sampling/analysis member of the device of the present invention. FIG. 6 illustrates the use of the sampling wand 17, held in a single hand 62 of the operator, to obtain a sample from a surface 60 suspected of bacterial contamination. In a preferred manner, the sampling/analysis member 15 is first inserted into the port 24 of the assay device 10. If a protective external seal has been provided with the sampling/analysis member, then the seal must first be broken and/or removed before the sampling wand 17 can be inserted into the port 24. As can be seen from FIG. 6, the sampling wand 17 is then removed from the inner chamber 40 of the sampling/analysis member 15. Once removed, the sampling wand 17 can be placed in close proximity to the surface to be sampled so that the sampling swab 27 contacts the surface. As will be discussed in more detail below, the sampling swab 27 is preferably packaged and sealed in the sampling/analysis member in a pre-wetted state. More preferably, the sampling swab 27 is pre-wetted with a solution of an extracting agent, preferably in an appropriate buffer to maintain the solution at a pH value in the range of 5.7 to 7.5. A preferred extracting agent is a cationic detergent.

Several suitable detergents or combination of detergents are known to those skilled in the art and include nonionic detergents such as Triton X-100, Tween 20, Tween 80, Nonidet P40, n-Undecyl Beta-D glucopyranoside; zwitterionic detergents such as n-hexadecyl-N,N-dimethyl-3-ammonio-1-propanesulfonate; and cationic detergents such as alkyltrimethylammonium bromides, benzalkonium chloride, cetyldimethyl-ethylammonium bromide, dodecyltrimethylammonium bromide, and cetyltrimethylammonium bromide. The concentration of detergent solution varies for each type of detergent and can range from 0.001–10% (wgt/vol). Particularly preferred detergent solution would contain benzalkonium chloride, or similar cationic detergent, at a concentration of 0.01–1% (wgt/vol).

In a most preferred embodiment, the sampling swab 27 is loaded with from 40 to 80 $\mu$L of the detergent solution, preferably 75 $\mu$L. The sampling swab 27 is of a size and composition such that the maximum loading of the swab would be approximately 100–125 $\mu$L of the detergent solution. With a preferred polymeric composition, the cylindrically shaped sampling swab 27 would be approximately 8 mm in diameter and 1.5–1.8 mm in height (dry). As expected for such an absorbent material, significant swelling would accompany the uptake of pre-wetting solution so that final dimensions at preferred loading levels would be on the order of 9–10 mm×2.5–3.5 mm.

It should be noted that, according to the present invention, the exact loadings and capacity of the sampling swab 27 are not absolute. What is important to the practice of the methods of the present invention is that the sampling swab, whatever its specific geometry, or its absolute capacity to absorb and hold a solution of an extracting agent, be loaded with a solution of such agent to a level that is somewhat below the saturation capacity of the swab material. The specific significance of this loading level will be addressed in more detail below.

As can be seen from the Figures, including FIG. 6, the sampling swab 27 is represented as having a regular cylindrical geometry. As should also be apparent to one of skill in the appropriate art, the use of a regular cylindrical geometry is for illustrative purposes only, and is not intended to limit the range of suitable geometries for the sampling swab 27 in the practice of the present invention. For example, it may prove to be advantageous to provide the sampling swab 27 in a geometry where the bottom surface of the swab cylinder that actually comes in contact with the surface to be sampled is not parallel to the top surface of the swab. In this regard, the bottom surface of the sampling swab 27 is angled downward. Thus configured, the sampling swab may be better able to reach less accessible portions of the surface to be sampled, such as corners or ridges or other surface irregularities, particularly where that surface is not perfectly planar and/or regular.

Once the sampling swab 17 has been used to collect a sample from the surface onto the sampling swab 27, the sampling wand 17 is returned to the sampling/analysis member 15 where the wand is re-inserted into the inner chamber 40 of the sampling/analysis member. When first reinserted, the sampling wand 17 can be returned to its original longitudinal position within the inner chamber 40 of the sampling/analysis member 15. In that position, the member 15 is in substantially the same arrangement as depicted in FIG. 5. In that arrangement, upper seal 29 remains undisturbed, and the contents of the reservoir 23 are intact.

Figure 7:
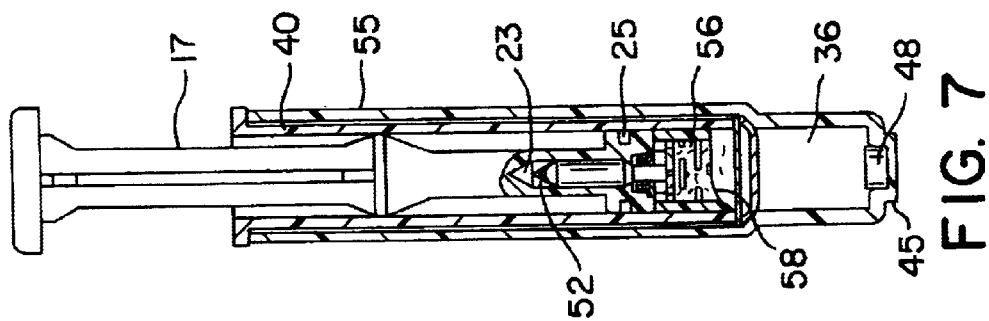
FIG. 7 is a cross-sectional view of the sampling/analysis member of the device of FIG. 1. illustrating the sampling wand in a first operative position within the sampling/analysis device.

FIG. 7 illustrates the sampling wand 17 moved longitudinally within the inner chamber 40 of the sampling/analysis member to a first operational position. In this first operational position, the sampling wand 17 has been moved downward so that the point 52 of the piercing member 53 moves upward, in a relative sense, piercing the sampling swab 27, upper seal 29, and releasing the contents of the reagent solution from the reservoir 23. The reagent solution thus released travels downward out of the reservoir 23 and diffuses through the sampling swab 27 and into the distal end of the inner chamber 40 of the sampling/analysis member 15. Preferably the reagent solution in the reservoir contains a neutralizing solution to counteract the effects of any residual cleaning agents, typically chlorine-based, present on the solid surface being sampled with the device of the present invention. In addition, the reagent solution also contains a buffering agent to maintain the solution at a pH value of approximately 7.5. The reagent solution can also contain non-ionic detergents such as Tween 80 and Triton X-100, or other species such as cyclodextrins, bovine serum albumin, and other suitable neutralizing species. As the solution diffuses through the sampling swab 27, it effectively rinses the sample obtained from the surface to be analyzed into the solution collected at the bottom of the inner chamber.

Figure 9:
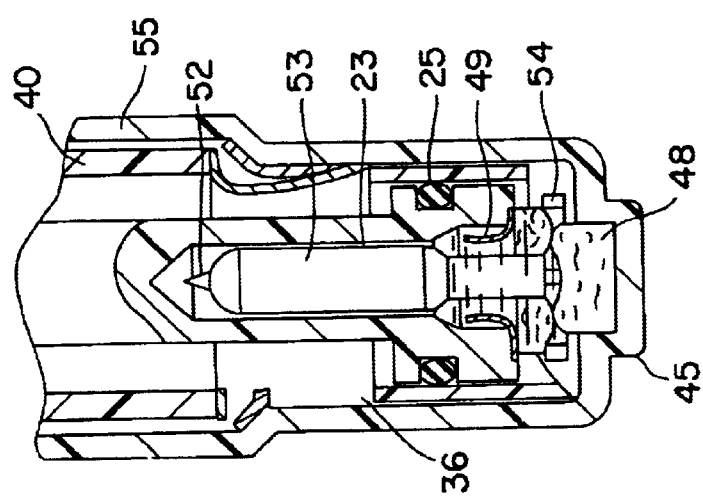
FIG. 9 is a magnified view of the distal end of the sampling/analysis member of the device of FIG. 1. with the sampling wand in a second operative position within the sampling/analysis device.
Figure 8:
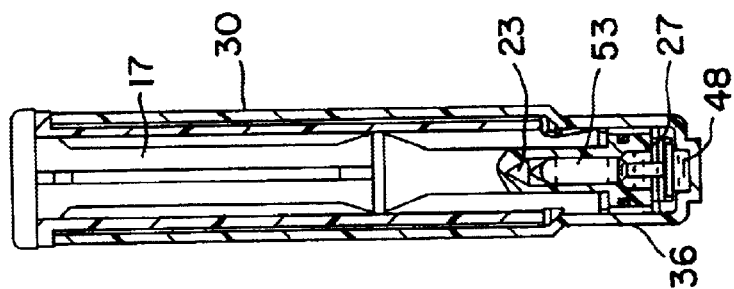
FIG. 8 is a cross-sectional view of the sampling/analysis member of the device of FIG. 1. illustrating the sampling wand in a second operative position within the sampling/analysis device.

From this first operational position, the sampling wand 17 may be urged further downward to a second operational position, as shown in FIG. 8, and in magnified detail in FIG. 9. In so moving, the cutting edge 58 of the cutting member 56 is forced to break through the first and, if present, second seals, 49 and 50, respectively. In doing so, the reagent solution from the reservoir, that has effectively removed from the sampling swab 27 any microbial species and/or chemicals derived therefrom obtained from the surface to be analyzed, is permitted to flow further downward through the inner chamber 40 and into the reaction well 36 at the distal end of the outer chamber 55. In returning the sampling wand 17 to the sampling/analysis member 15, and moving the sampling wand downward to the first and second operational positions, the outer surface of the outer chamber 55 or of the sampling wand 17 may be provided with external markings, such as circumferential rings, indicating to the operator the appropriate positions to which to move the distal end of the sampling wand 17. As described immediately above, the sampling wand 17 may be moved downward through the chambers 40 and 55 of the sampling/analysis member 15 in a step-wise progression. However, it is also possible to move the sampling swab downward in a single movement without pausing between the first and second operational positions.

As the reagent/sample solution collects in the reaction well 36 of the outer chamber 55, the solution comes into contact with the reagent disc 48. As a result of this contact, the reagents contained therein are rehydrated. In rehydrated form, the reagents are free to react with the extracellular ATP released from the bacterial species collected from the sampled surface. Once allowed to react, the ATP, if present, will lead to the production of light (luminescence). The reaction, in normal practice, occurs within the reaction well 36, inserted in close proximity to the detector of the luminometer 20 of the present invention. Due to the kinetics of the reaction and the solubility of the reagents, at low ATP concentrations optimal luminescent intensity is normally observed within 20–60 seconds of commencement of the chemiluminescent reaction, and possibly within 30–40 seconds. Using techniques known to one of ordinary skill in the appropriate electronics arts, it is possible to design the detector and display circuitry of the luminometer 20 to process the output signal so as to report an optimized reading obtained most likely in that 30–40 second time window of the luminescent reaction.

Figure 10:
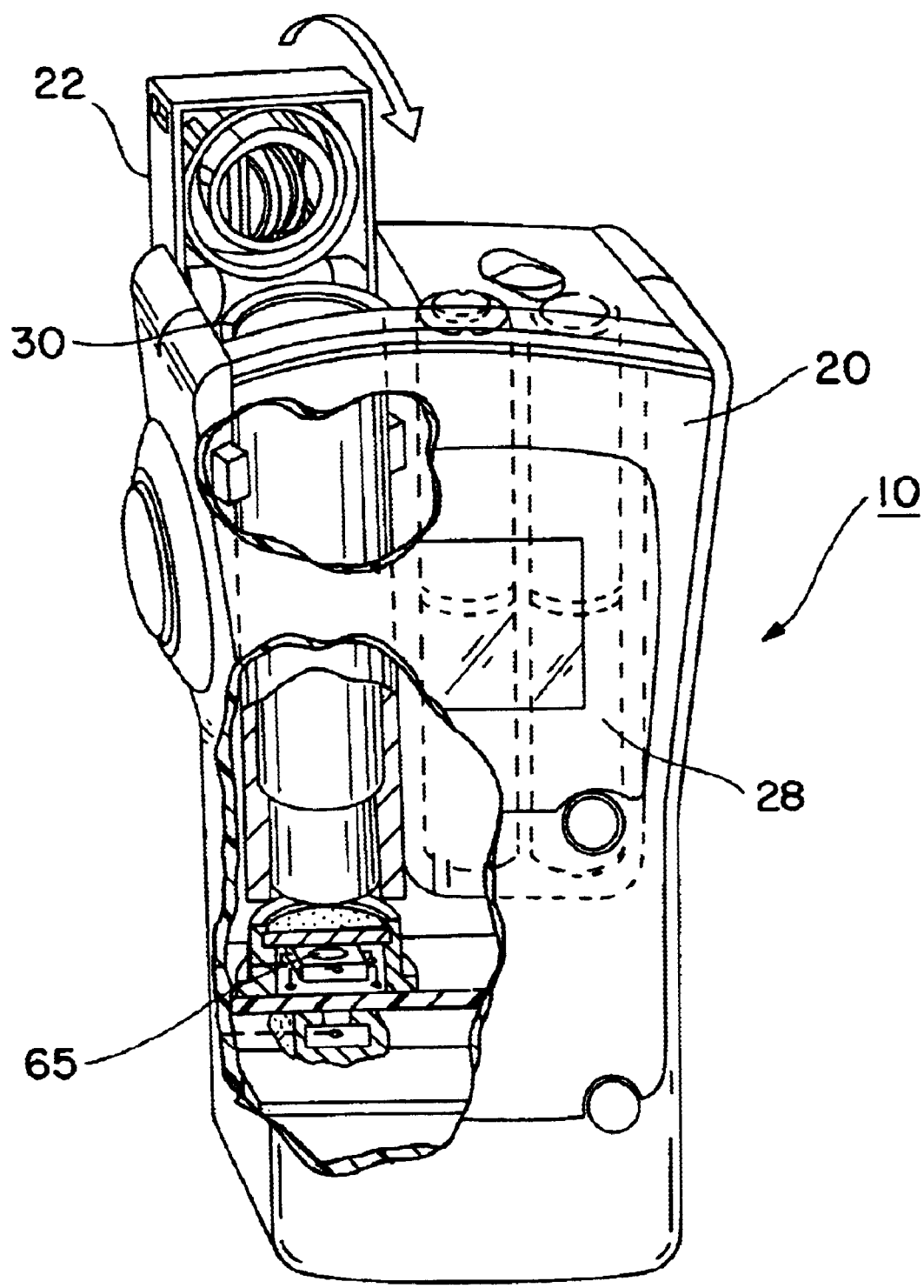
FIG. 10 is a partial cut-away perspective view of the luminometer of the device of FIG. 1.

By reference to FIG. 10, it is possible to see, via the cutout views in the Figure, the position of the reaction well and, more specifically, the reagent disc cavity 45, relative to the detector circuitry 65. The bottom wall of the reagent disc cavity 45 is transparent so that light from the chemiluminescent reaction taking place within the reaction well 36 is permitted to escape the reaction well and reach the detector 65. Also important to note here is that the only emitted light reaching the detector emerges from the reagent disc cavity and not the surface of the sampling swab 27, which surface is too far removed from the detector and chemiluminescent reagents to produce light that contributes to the analytical signal that is eventually reported to the operator on the display screen 28 of the luminometer 20.

Referring back now to the individual components of the sampling/analysis member 15, it is useful to note certain characteristics and operational specifications of these components. Turning first to the sampling swab 27, successful and optimal practice of the present invention places certain requirements on the material used for the swab 27. As can be seen from the discussion of the prior art provided above, the vast majority of the prior art sampling and/or analysis devices disclosed therein utilize a "Q-Tip®" type sampling swab. As such, the swabs of the prior art were composed primarily of cotton or other fibrous materials, whether natural or man-made, or a combination thereof. Although such materials can be utilized in a variety of applications, the present inventors have determined that practice of the present invention can be optimized through selection of the proper material for use as the sampling swab 27. Toward this end, the preferred material for use as the sampling swab is polymeric in nature, as opposed to the fibrous material that predominates in the prior art. Use of a polymeric material provides a number of advantages in the fabrication of the swab and also its incorporation into the sampling wand 17. First of all, a suitable polymeric material may be cast or formed into an appropriate geometry that facilitates contact of the swab with the surface to be analyzed for the presence of materials derived from microbial organisms, or other analytes of interest. As described above, the preferred geometry for the sampling swab 27 of the present invention provides a flat surface that maximizes surface area contact between the swab and the surface to be analyzed. Use of the preferred alternative geometry wherein the bottom surface of the swab is not parallel to the top surface further increases effective sampling surface area for the swab for a given cylindrical radius, but also provides a relatively sharp edge that can be effective in reaching irregularities in the sampled surface. A further advantage of an appropriate polymeric material is that it can be sterilized by steam and/or pressure, or by gamma irradiation. This is a characteristic that is essential given the primary uses of the device of the present invention.

Use of a polymeric material for the sampling swab 27 makes it possible to select and control optimal physical and chemical properties of the swab that enhance the effectiveness of the practice of the present invention. For example, as discussed above, the sampling swab 27 is pre-wetted, preferably with a detergent extractant solution. It is important to effective sampling of a surface to be analyzed that the sampling swab be pre-wetted with solution at a loading that is somewhat below the saturation capacity of the swab material. With a polymeric material as the sampling swab, it is possible to fabricate the swab with specific densities and internal pore sizes so as to be able to achieve specific fluid loading characteristics, and to insure that these characteristics are met uniformly both throughout the swab and also from one swab to the next. The inventors have determined that a particularly preferred type of polymeric material is composed of the reaction product of polyvinyl alcohol and an aldehyde to produce a polyvinyl acetal. In this regard, reference is made to U.S. Pat. No. 4,098,728, the disclosure of which, herein incorporated specifically by reference, teaches methods for the preparation of such polymeric species. However, based on the disclosure contained herein, one of skill in the appropriate art will recognize that other polymeric materials, such as forms of polyvinyl alcohol, will serve as well, provided these materials possess the desired physical and chemical properties.

The present inventors have determined that the Merocel® brand of polymeric films, available from Medtronic Merocel, of Mystic, Conn., is particularly well suited for use as the sampling swab material. The Merocel® brand is commercially available in a number of grades with a range of physical properties across the grades. An alternative source of polymeric materials suitable for use in the methods and apparatus of the present invention is Hydrofera, of Willimantic, Conn. The preferred grade of Merocel® for the sampling swab is sold under a product designation of CF200. Typical properties for such a product are provided in Table 1, below.

TABLE 1

Merocel ® CF200

| Property | Value |
|---|---|
| Density (dry) | >0.10 g/cc |
| Average pore size | 0.2 mm |
| Pore size range | 0.004–0.4 mm |
| Void Volume | ≦90% |
| Absorbency time ASTM D1117-80 | <5 sec. |
| Absorptive capacity (g water/g material) | <10 times |
| Retained capacity | 6–8 times |

The Merocel® CF200 offers a number of advantages over alternative swabbing materials heretofore used in the prior art. Chemically speaking, the material is highly resistant to chemical attack, including attack from fluids with both high and low pH (basic and acidic, respectively). Thus, the film is an extremely durable material. This is particularly advantageous in a component of the device that may have a relatively long expected shelf life. The mechanical durability of the swab is also superior to prior art swabbing materials. Unlike "Q-Tip®" type swabs composed of fibrous materials, polymeric swabs are not prone to unraveling or loss of strands of the fibrous material from the swab tip. In addition, polymeric swabs are far less likely than cellulose sponges, the primary alternative to fibrous swabs in the prior art, to shredding or crumbling at the edges. As will be illustrated below, an important characteristic of the preferred material for the sampling swab 27 is that the absorbent nature of the material provides nearly instantaneous wicking when in contact with moisture. This greatly facilitates the sampling process, described immediately below, whereby bacterial organisms are removed from a surface to be sampled.

In actual use, as illustrated in FIG. 6, the sampling wand 17, after extraction from the sampling/analysis member 15, is positioned above the surface to be analyzed so that the sampling swab 27 at the distal end of the sampling wand 17 is in contact with the surface. In a preferred method of use, the pre-wetted sampling swab is pressed to the surface to be analyzed with sufficient force that, as the sampling swab 27 is moved across the surface, the detergent extractant solution with which it has been pre-wetted is expelled from the swab and spread over the surface to be analyzed. The sampling wand 17 is then wiped again across the now wet surface. The absorptive capacity of the Merocel® CF200 swab is such that the swab effectively reabsorbs the moisture from the surface to be sampled. The microbial cells taken up from the surface in this manner have thus already been in contact with the extracting agent and the process of cell disruption to release cellular ATP has already begun. Thus, when the sampling wand 17 is returned to the sampling/analysis member 15, and the sampling wand is forced downward within the chambers of the analysis structure 30, the release of ATP from the bacterial cells should be largely accomplished and the resulting solution should require less time before reaction with the chemiluminescent reagents to produce the emitted light that constitutes the analytical signal.

Although the Figures and the description provided above are primarily directed to the use of the device and methods of the present invention in the sampling of solid surfaces, it should be noted that the device and methods disclosed herein are particularly suited to adaptation for use with other types of samples and alternative methodology. For example, the device of the present invention can readily be used to sample for materials indicative of the presence of microbial species in liquid samples and not just on solid surfaces. To obtain a sample from a liquid source using the sampling wand 17 of the present invention, the swab 27 on the sampling wand should contain an effective amount of an extracting agent such as a detergent. The swab 17 can be loaded with a detergent solution simply by contacting the swab to an appropriate solution. Alternatively, the swab can be further treated after contacting a detergent solution by evaporation of the solvent from the detergent solution, leaving behind the solute detergent species. The specific characteristics of the polymeric material of which the swab is comprised are particularly well suited for this practice due to the large void volume within the polymer and the resulting absorptive capacity of the swab. Furthermore, the large internal surface area within the polymeric material arising from the large void volume provides optimal conditions for the rapid mixing of liquids with the dry reagents, such as a detergent, loaded into the swab.

When sampling a liquid, the sampling wand 17 can simply be contacted with the liquid, and the high absorptive capacity of the swab 27 should result in an almost instantaneous wicking of the liquid to be sampled into the swab. Alternatively, the liquid to be sampled can be transferred directly to the swab 27 by a dropper, pipette, or other suitable transfer means. If necessary to acquire a sample of sufficient volume, the size of the sampling swab 27 can be increased. Because it is important for the swab material to retain capacity to absorb additional fluid when sampling a liquid, it is necessary to avoid pre-wetting the swab 27 to absorptive saturation or the swab will be unable to retain a sufficient volume of the sampled liquid. Therefore, care must be taken when wetting the swab 27 when it is the intention of the operator to use the swab in a pre-moistened state. It can be preferable, then, to utilize the swab 27 where the solvent from the detergent solution is evaporated away.

It should be recognized that one of the potential problems associated with sampling liquids is that the analyte of interest, for example bacterial cells, may not be present at sufficiently high concentration levels to provide a meaningful sample. This situation is not unusual when assaying a liquid sample for microbial content. However, it is possible to pre-concentrate the microbial species in the liquid by filtering the liquid through an appropriate filter, such as one with a filter size of approximately 0.2 microns ($\mu$m). After the filtering step, the sampling wand 17 can be swiped across the surface of the filtering medium to acquire the concentrated sample. The sampling wand can then be used in a manner consistent with the sampling of solid surfaces, as described above.

Methods for use of the sampling device of the present invention can also be readily adapted to more conventional techniques associated with microbial assays. For example, a sample, whether from a liquid or from a solid surface, can be acquired as described above. However, instead of subsequent reaction and analysis in the luminometer device 20 of the present invention, the sample can be transferred from the sampling wand 17 to a conventional culturing medium such as an agar plate. Once transferred to the culture medium, standard procedures for detection of microbial growth can be utilized. In order to use the device of the present invention in such a manner, the sampling swab 27 would be prewetted with a sterile saline solution instead of with a solution of an extracting agent. The contents of the reagent reservoir 23 within the sampling wand 17 preferably would also be a saline solution, or other such solution as would be consistent with retention on the microorganism's viability. The sampling wand would then be pressed against the surface of the culture medium to express the sample from the sampling swab 27 to the medium. Alternatively, the container of the culture medium could be adapted with a structure to pierce the upper seal 29 in the sampling wand to release the saline solution stored therein. In this manner, the release of the saline solution would rinse the sample from the sampling swab 27 onto the culture medium. This alternative to the practice of the present invention offers additional advantages in that the culture medium can be selected to be specific for certain microbial species, or otherwise adapted to more specific assay techniques. In an alternative embodiment, the methods of the present invention can be adapted to include transfer of a sample to a vessel, other than the analysis structure 30, wherein the vessel contains affinity reagents such as antibodies to a specific species. The affinity reagents permit only certain microbes to be retained within the vessel. These specific microbes can then be transferred to an appropriate culture medium for growth and subsequent analysis.

The reactant mixtures typically used for assays of the type involved in the practice of the present invention, including luciferase, luciferin, and magnesium ion, are usually sold as a single combined reagent system, not as individual reagents. The luciferase must be within a suitable pH of approximately 7.0 to 8.5 in order to be effective, usually achieved by employment of a buffer system. An appropriate buffer system for the reactant solution would be one comprised of tricine, N-[tris(hydroxymethyl)methyl]glycine (($HOCH_2)_3C$—$NHCH_2COOH$), preferably at a concentration of 50 mM, sufficient to maintain the pH of the reactant solution in the range of 7.8 pH units. Alternatively, an appropriate buffer would be N-2-hydroxyethylpiperazine-N'-2-ethanesulfonic acid (HEPES), also capable of maintaining the solution at a pH value of approximately 7.5–7.8. If the proper pH is not maintained, the reaction will not work efficiently, and the results will be erroneous. However, luciferase is unstable while in solution, and will degrade, particularly at higher temperatures. Generally, at room temperature, the luciferase solution will remain effective for a period of hours whereas, at near freezing temperatures, the luciferase solution will last for a period of days. In addition, luciferin in solution is light sensitive. Light causes the dissolved luciferin to degrade, forming chemical species that have an inhibitory effect on the luciferin/luciferase reaction, potentially resulting in false negatives. To prevent degradation, the luciferin and luciferase can be dried and protected from light. Prior art methods for drying include, but are not limited to, freeze-drying and lyophilization. When ready to use, the dried luciferin and luciferase are dissolved in water containing an appropriate buffer to form an aqueous solution having the proper pH.

To address the problem of reagent stability, the present inventors utilize a reagent disc 48, loaded with the chemiluminescent reactants needed to produce the analytical signal (chemiluminescence). The present inventors have determined that a preferable material from which to construct the disc is a polymeric material, also available from Merocel® (under the CF50 product designation). A summary of the properties of such a grade of material is provided below in Table 2.

TABLE 2

Merocel ® CF50

| Property | Value |
| --- | --- |
| Density (dry) | 0.049 g/cc |
| Average pore size | 0.95 mm |
| Pore size range | 0.2–1.2 mm |
| Void Volume | 95% |
| Absorbency time ASTM D1117-80 | <5 sec. |
| Absorptive capacity (g water/g material) | <21 times |
| Retained capacity | 16 times |

As discussed above, the inherent chemical and mechanical stability of the polymeric material is ideally suited for use as a medium on which to load the chemiluminescent reagents for the practice of the present invention. A number of commercial enterprises market luciferin-luciferase reagent kits for use in chemiluminescent reaction assays. One that the inventors have found to be particularly well suited for the practice of the present invention is the "Firelight®" luciferin-luciferase reagent kit provided by Analytical Luminescent Laboratories (ALL) of Sparks, Md. Although ALL provides a number of pre-prepared reagent kits, the present inventors have found that a reagent mixture based on ALL catalog #2005 is particularly preferred, with the only modification from the commercially available catalog formulation being that the luciferase component of the formulation is present at twice the amount in the catalog formulation. This provides for a greater intensity of luminescence, and faster reaction kinetics.

In the preparation of the reagent discs 48, the reactant concentrate is loaded, preferably drop-wise, onto the Merocele CF50, obtained in pre-sterilized sheets. The coated sheets are then dried at ambient temperatures under a vacuum, and the reagent discs are cut from the sheets in an appropriate size and shape. Alternatively, discs may be cut first and then loaded with appropriate reagent solution. When loaded in such fashion with the reagent mixture, reagent discs, approximately 6 mm in diameter and approximately 1.5 mm in height, carry approximately 0.5 mg of the dried reactant mixture.

Use of the polymeric material as a medium onto which to load the chemiluminescent reactants offers significant advantages over prior art methods. To begin with, as discussed briefly above, aqueous solutions of luciferin-luciferase at concentrations suitable for typical assay procedures are relatively unstable and cannot be used more than a day after preparation without significant loss of emission intensity, and then only after a recalibration of the emission signal as a function of ATP standard concentration. The recognized prior art solution to the problems associated with instability of aqueous solutions of the reagents is to prepare the reagent mixture in a lyophilized, or freeze dried, form, which composition is then typically coated on the inner surfaces of a reaction vessel. Direct loading onto the durable polymeric material eliminates the need for the lyophilization step in the preparation of the reactants, and also provides for more readily achieved rehydration of the reagents once the reactant disc 48 is in contact with the sample solution. This is due, in part, to the relatively large internal surface area of the preferred polymeric material (see Table 2, above) that provides for almost instantaneous mixing of the reservoir solution with the reagents in the reagent disc 48.

The device and methods of the present invention are also adaptable to additional procedures to enhance, in general, the effectiveness of the assay. For example, it is possible to significantly increase the sensitivity of the assay procedure by utilizing a chemical pre-concentration step. In this manner, a microbial sample is collected according to the procedures described above. Instead of immediately transferring the acquired sample to the analysis structure 30, the sample is transferred to a suitable reaction vessel wherein, according to procedures such as those disclosed in U.S. Pat. No. 5,902,722, the specific disclosure of which is hereby incorporated by reference, all nucleic acids in the sample are converted to inorganic phosphate. By use of such a chemical pre-concentration step, it is theoretically possible to achieve amplification by a factor of $10^6$, or more. Thus, a technique that normally has a threshold sensitivity requiring the presence of from 1,000 to 10,000 microbial cells to generate an analytical signal can detect the presence of a single cell.

In an alternative embodiment of the present invention, the chemiluminescent reagent formulation loaded onto the reactant discs 48 can be prepared with an additional ingredient that provides superior results in the chemiluminescent assay of the present invention. This additional reagent is trehalose, a common disaccharide.

Macromolecular compounds, especially proteins and polypeptide-containing compounds, commonly exist in their naturally occurring hydrated state in the form of complex, three-dimensional folded conformations generally known as tertiary structures. Very frequently, the activity of the compound, whether as an enzyme, antibody, antigen, flavorant, fluorescent, gelling agent, etc., is critically dependent on the tertiary structure and is severely reduced or even eliminated if the structure is disturbed, even though the chemical empirical formula of the compound may not have changed. This is a very serious problem when the protein is required in a dry state for storage.

In order to combat this problem various solutions have been proposed. In the prior art, enzymes for dry immunoassay kits have been protected in liposomes. Trehalose, a-D-glucopyranosyl-a-D-glucopyranoside, is a naturally occurring non-reducing disaccharide that has previously been associated with cell protection. It is known that some organisms, both plant and animal, can resist desiccation to very low levels of body water during drought conditions. These organisms include brine shrimps cysts (*Artemia salina*), the resurrection plant (*Selaginella lepidophylla*) and bakers yeast (*Saccharomyces cerevisiae*). They all share, as a common feature, the presence of large amounts of trehalose in their cells. A body of work in the prior art exists on the effects of various carbohydrates including trehalose on the stabilization of cell membranes during freezing and dehydration. This work shows trehalose to be significantly superior to other carbohydrates in protecting cellular organelles from the deleterious effects of the loss of bound water.

Figure 11:
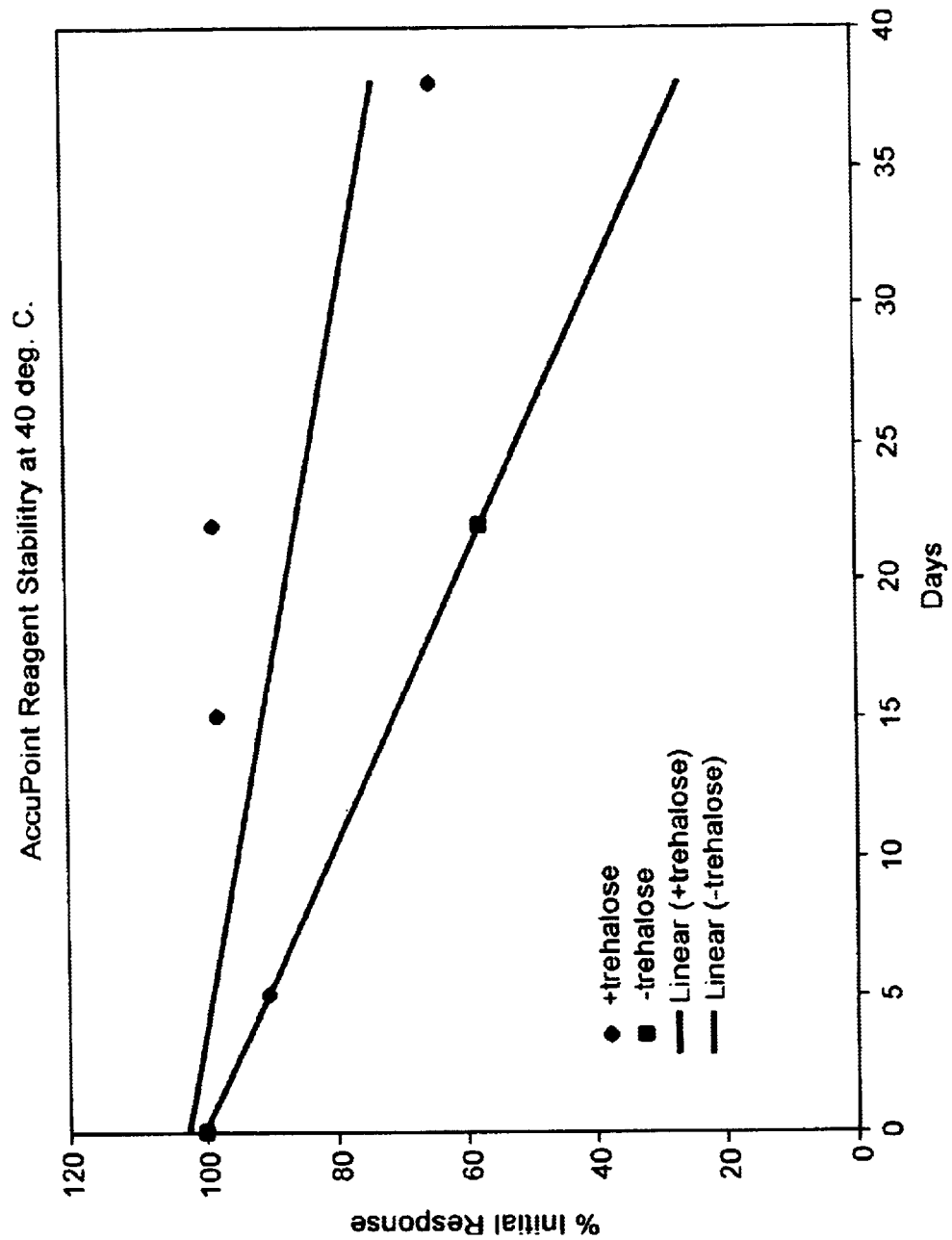
FIG. 11 is a plot of relative luminescent intensity for reactant mixtures prepared with (♦) and without (■) trehalose in the reactant loading solution for use with the device of FIG. 1.

It is recognized in the prior art that trehalose will stabilize delicate materials while they are freeze-dried. Freeze drying as a technique was devised as being the only way certain sensitive materials can be handled. Ordinary drying at ambient or elevated temperature and at atmospheric or reduced pressure causes irreversible degradation of very many such substances, so much so that it has been accepted that sensitive proteins must not be dried at ambient temperature. In freeze-drying, the water is removed under high vacuum from the solid material. In this way, problems such as liquid film denaturation of proteins and thermal instability can be avoided. However, the requirement for freeze-dry preparation of reagents adds considerable cost and complexity to the process of reactant preparation. It is an advantage of the practice of the present invention that such processes are not needed to maintain reagent stability. However, the present inventors have discovered that addition of trehalose to the loading solution of the chemiluminescent reactant mixture, at levels approaching the saturation solubility of trehalose in the solution, while providing a measurable stabilization effect as illustrated in FIG. 11, can also provide up to a doubling, or more, of the biochemical activity of the luciferase component of the reagent mixture. In practical terms, this means that considerably less of the relatively expensive chemiluminescent reagents need to be used in the reactant mixture. The presence of trehalose and its effect on the luciferase activity also provides for an enhancement of the emission signal and, thus, a potential increase in the sensitivity of the assay procedure.

Figure 12:
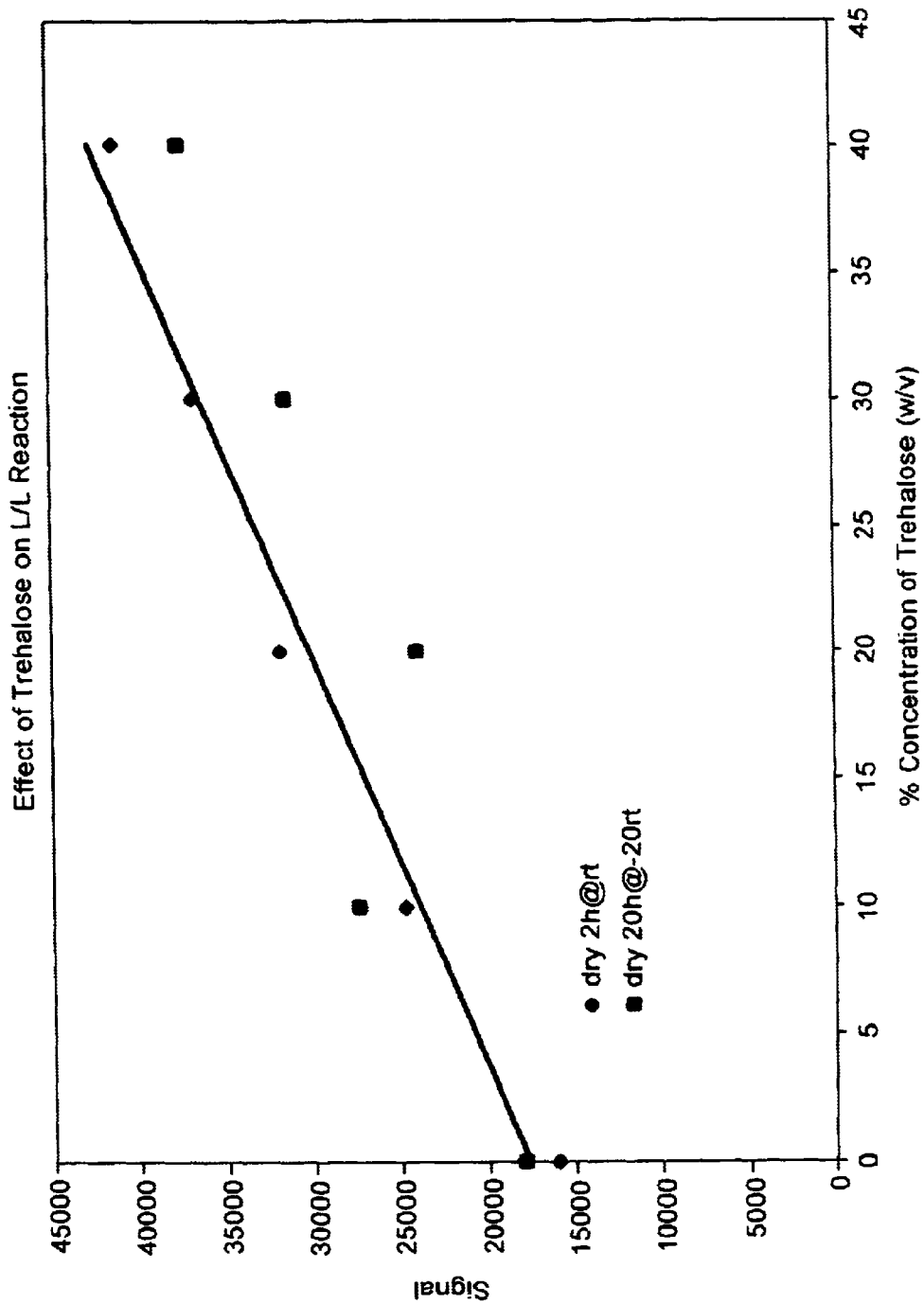
FIG. 12 is a plot of luminescent intensity as a function of the concentration of trehalose in the reactant solution for use with the device of FIG. 1.

When the reagent mixture includes an effective amount of trehalose, by way of example and without specific limitation, the 6 mm×1.5 mm reagent disc has a total loading of approximately 4 mg. At this loading, as can be seen from FIG. 12, observed luminescent intensities were more than twice that obtained from the same loading of reagents without the trehalose.

In addition to the luciferase reactant system disclosed above, it is possible for the device and methods of the present invention to be adapted to assays of additional analytes of interest. In order to achieve this, the reactant mixture would be modified to comprise an alternative enzyme to luciferase, where that enzyme would be capable of oxidizing a specific substrate of interest. Examples of such substrates for which specific enzymes are available would be sugars such as glucose and galactose; lipids such as fatty acids and cholesterol; amino acids and other amines; pyruvate; nicotine adenide dinucleotide (NAD) and derivatives; and alcohols. In general, the substrate of interest would be oxidized by the enzyme to generate hydrogen peroxide, $H_2O_2$, as one of the reaction products. The peroxide, in turn, can react with the specific reactant system in the reactant disk 48, and generate a luminescence signal detectable in the luminometer 20 of the present invention. Thus, by changing the reactant mixture loaded onto the reactant disc 48, it is possible to adapt the device and methods of the present invention to assays for a wide range of analytes of interest.

A recognized problem associated with chemiluminescent assays of the type disclosed herein, as alluded to in the general discussion above, is that the activity of the chemiluminescent reagents necessary for the assay procedures is sensitive to inhibition by some commonly encountered substances. Of particular importance among these inhibitory substances is the chlorine used in typical cleaning and sanitizing formulations. The presence of residue from chlorine-based cleaners on a surface to be analyzed for the presence of bacterial contamination could lead to false negative results from the assay procedure of the present invention. The likelihood of such an erroneous result is enhanced by the fact that chlorine-based cleaners are frequently used to clean the type of surfaces most likely to be subject to the analyses of the present invention. However, even after the use of such cleaners to ostensibly sanitize, for example, a food preparation surface, it is possible for viable bacterial cells to remain on the surface. In such a case, however, it is likely that chlorine residue from the cleaner would inhibit the luciferin/luciferase-ATP reaction, effectively masking the presence of persistent bacterial contamination, and producing a false negative result. Thus, a food preparation facility, suspecting persistent bacterial contamination of their food preparation surfaces, and expecting the application of the present invention, perhaps by municipal authorities, to assess the hygiene of their facility, could utilize a chlorine-based cleaner on the food preparation surface. Although such a cleaner would have some sanitizing effect on the food preparation surface, it is unlikely that its use would be completely effective. However, the inhibitory effect of residual chlorine species from the cleaner would produce a result that would be erroneously read as indicative of a clean surface, free from bacterial contamination. Thus, the purpose of the practice of the present invention would be effectively thwarted.

An alternative embodiment to the present invention provides a procedure to determine whether residual inhibitory species, such as chlorine or other residue from a sanitizing agent, or other treatment, exist on a surface to be analyzed sufficient to cause a false negative result for a bacterial assay according to the present invention. The reagent reservoir 23 provided in the sampling wand 17 of the present invention preferably comprises a neutralizing species in solution. See discussion above. However, it is possible to prepare the reagent solution for the reservoir 23 to include instead a precisely known quantity of ATP. Thus, use of such a sampling wand in the practice of the present invention, without contacting the sampling swab with the surface to be analyzed, would provide an emission signal in the luminometer of the present invention that would be indicative of the known amount of ATP included in the reagent solution stored in the reservoir 23. If this sampling swab, with the reagent solution modified to include a known amount of ATP, is used to first swab a surface to be analyzed for the presence of microbial contamination, then the detected luminescence intensity should be the sum of the intensity from the microbial ATP present in the sample and the known ATP from the reagent solution. If, however, the assay result obtained is significantly below that expected from the known amount of ATP present in the reservoir solution, then this would indicate inhibition of the chemiluminescent reaction by a species such as residual chlorine on the sampled surface. Thus, the operator would know that use of the conventional sampling/analysis member would be fruitless, as it would likely provide a false negative result. The operator would then have to wait to obtain a meaningful hygiene determination until after the residual inhibitory species is removed from the surface to be analyzed. Thus, the apparatus of the present invention could be provided with both versions of the sampling/analysis member. An operator would first use the embodiment containing the known amount of ATP and, only upon measuring a luminescence signal appropriate for the known amount of ATP in the reagent reservoir, would the operator proceed to use the conventional embodiment of the sampling/analysis member 15 to test the hygienity of the sampled surface.

What is claimed is:

1. A method for assaying for the presence of an analyte of interest, the method comprising the steps of:
   a.) providing a sampling swab containing a first reagent and being mounted on a wand on a bottom surface and adapted for sampling on a top surface, the wand having a reservoir adjacent the bottom surface of the sampling swab, the reservoir containing a second reagent as a solution wherein the second reagent is separated from the sampling swab by a seal on the reservoir of the wand;
   b.) providing an analysis structure comprising a receptacle for receiving the wand, the analysis structure having a piercing member which can contact the sampling swab;
   c.) contacting a surface to be analyzed with the top surface of the sampling swab so as to obtain a sample of at least a portion of the analyte of interest, if any, present on the surface;
   d.) inserting the sampling swab into the analysis structure so that the piercing member is adjacent the top surface of the sampling swab opposite the reservoir; and moving the sampling swab toward the piercing member in the analysis member to contact the top surface of the sampling swab with the piercing member to break the seal so that the second reagent contacts the sampling swab and transfers the sample from the sampling swab to the analysis member so that the sample contacts a reactant mixture in a reaction well located at a bottom of the receptacle and having a transparent wall to induce a chemiluminescent reaction; and inserting the analysis structure into a hand-held luminometer designed to accept the analysis structure so that when the sampling swab is inserted into the analysis structure, the pierced sampling swab is removed from a detector; and
   e.) measuring an emission of chemiluminescent radiation from the reactant mixture and sample in the reaction well to indicate the presence or absence of the analyte of interest in the sample.

2. The method of claim 1, wherein the analyte of interest comprises cellular material.

3. The method of claim 2, wherein the reactant mixture comprises a luciferase/luciferin system.

4. The method of claim 3, wherein the reactant mixture comprises a firefly luciferase/luciferin system.

5. The method of claim 3, wherein the reactant mixture comprises a recombinant luciferase/luciferin system.

6. The method of claim 2, wherein the reactant mixture comprises reagents that break down all nucleic acids present in the sample to inorganic phosphates and convert the inorganic phosphates to adenosine triphosphate (ATP).

7. The method of claim 2, wherein the first reagent solution is a detergent.

8. The method of claim 7, wherein the second reagent is a rinsing solution.

9. The method of claim 7, wherein the detergent is benzalkonium chloride.

10. The method of claim 9, wherein the second reagent is a rinsing solution.

11. The method of claim 1, wherein the cellular material is derived from microbial cells.

12. The method of claim 1, wherein the first reagent is a sterile saline solution.

13. The method of claim 12, wherein the second reagent is a rinsing solution.

14. The method of claim 1, wherein the first reagent is a wetting solution.

15. The method of claim 14, wherein the second reagent comprises a breaking reagent.

16. The method of claim 1, wherein further in step a, the first reagent is a solution and is provided on the sampling swab by contacting the sampling swab with the first reagent solution so that the sampling swab absorbs a volume of the first reagent solution corresponding to no more than 50% to 80% of a saturation loading for the sampling swab.

17. The method of claim 1, wherein the first reagent is a solution which includes a solvent and a reagent and wherein the first reagent solution is provided on the sampling swab by contacting the sampling swab with the first reagent solution and then evaporating a solvent from the first reagent solution.

18. The method of claim 1, wherein the analyte of interest is present in a liquid substance.

19. The method of claim 18, wherein prior to step c, the method includes the additional step of filtering the liquid substance through a filter medium effective to remove a microbial species from the liquid substance on the filter medium and then contacting the microbial filtrate with the sampling swab.

20. The method of claim 1, wherein the receptacle contains a culture medium suitable for promoting microbial cell growth.

21. The method of claim 1, wherein the analyte of interest comprises a species that can be oxidized by the action of an enzyme to yield an oxidized form of the species and hydrogen peroxide.

22. The method of claim 21, wherein the reactant mixture comprises an enzyme which oxidizes the analyte of interest in the sample in the receptacle to an oxidized form and hydrogen peroxide, and compounds capable of reacting with hydrogen peroxide to produce a chemiluminescence emission.

23. The method of claim 1, wherein the analyte of interest is selected from the group consisting of sugars, lipids, alcohols, amino acids, amines, and the reduced form of nicotine adenide dinucleotide (NADH).

24. The method of claim 1, wherein the receptacle contains an immunospecific species capable of binding to the analyte of interest.

25. The method of claim 24, wherein the immunospecific species is bound to a solid surface within the receptacle.

26. The method of claim 25, wherein the immunospecific species is bound to microspheres.

27. The method of claim 24, wherein the method involves the additional step of removing all species present in the receptacle that are not bound to the immunospecific species before contacting the sample with the reactant mixture.

28. The method of claim 24, wherein the immunospecific species is an antibody to the analyte of interest.

29. The method of claim 24, wherein the analyte of interest is an antibody.

30. The method of claim 24, wherein the immunospecific species is an antigen to the analyte of interest.

31. The method of claim 1 wherein the reaction well is sealed by a second seal, and wherein in step d.), the piercing member is moved toward the second seal and breaks the second seal so that the sample contacts the reactant mixture in the reactant well of the receptacle.

32. A method for assaying for the presence of an analyte of interest, the method comprising the steps of:
   a.) providing a sampling swab containing a first reagent and having a bottom surface mounted on a wand and a top surface adapted for sampling a surface, the wand having a reservoir adjacent the bottom surface of the sampling swab and containing a second reagent as a solution, wherein the second reagent is separated from the sampling swab by a first seal between the bottom surface of the sampling swab and the reservoir of the wand;
   b.) providing an analysis structure for receiving the wand, the analysis structure having a piercing member and a reaction well at a bottom of the analysis structure and having a transparent bottom wall, wherein the reaction well is sealed by a second seal;
   c.) contacting a surface to be analyzed with the top surface of the sampling swab so as to obtain a sample of at least a portion of the analyte of interest, if any, present on the surface;
   d.) inserting the sampling swab into the analysis structure so that the piercing member is adjacent the top surface of the sampling swab opposite the reservoir and moving the sampling swab in the analysis structure toward the piercing member to contact the top surface of the sampling swab with the piercing member to break the first seal so that the second reagent contacts the sampling swab and transfers the sample from the sampling swab to the analysis structure and continuing to move the sampling swab and the piercing member toward the reaction well so that the piercing member breaks the second seal and so that the sample moves into the reaction well and contacts a reactant mixture in the reaction well of the analysis structure to induce a chemiluminescent reaction, and inserting the analysis structure into a hand-held luminometer designed to accept the analysis structure so that when the sampling swab is inserted into the analysis structure, the pierced sampling swab is removed from a detector; and
   e.) measuring an emission of chemiluminescent radiation from the reactant mixture and sample in the reaction well to indicate the presence or absence of the analyte of interest in the sample.

* * * * *